(12) United States Patent
Niestroj et al.

(10) Patent No.: US 7,592,467 B2
(45) Date of Patent: Sep. 22, 2009

(54) INHIBITORS OF PROLYL ENDOPEPTIDASE

(75) Inventors: Andre Johannes Niestroj, Sennenwitz (DE); Ulrich Heiser, Halle/Saale (DE); Hans-Ulrich Demuth, Halle/Saale (DE); Susanne Aust, Halle/Saale (DE)

(73) Assignee: Probiodrug AG, Halle (Saale) (DE)

( * ) Notice: Subject to any disclaimer, the term of this patent is extended or adjusted under 35 U.S.C. 154(b) by 48 days.

(21) Appl. No.: 11/400,582

(22) Filed: Apr. 7, 2006

(65) Prior Publication Data

US 2006/0229357 A1    Oct. 12, 2006

Related U.S. Application Data

(60) Provisional application No. 60/670,165, filed on Apr. 11, 2005.

(51) Int. Cl.
- *C07D 333/12* (2006.01)
- *C07D 333/22* (2006.01)
- *C07D 307/46* (2006.01)
- *A61K 31/341* (2006.01)
- *A61K 31/381* (2006.01)

(52) U.S. Cl. .................. 549/72; 549/488; 514/444; 514/448; 514/461

(58) Field of Classification Search .................. 549/72
See application file for complete search history.

(56) References Cited

U.S. PATENT DOCUMENTS 5,030,647 A * 7/1991 Miao et al. .................. 514/414

FOREIGN PATENT DOCUMENTS

EP    0 709 373 A1    5/1996

OTHER PUBLICATIONS

Concise Encyclopedia Chemistry (1993) Walter de Gruyter Berlin-New York.*
A. Maureen Rouhi, Chemical & Engineering News, Feb. 24, 2003, pp. 32-35.*
RN 160560-03-2; CAPLUS search; retrieved on Mar. 24, 2008.*
RN 860697-48-9; CAPLUS search; retrieved on Mar. 24, 2008.*
RN 855470-65-4; CAPLUS search; retrieved on Mar. 24, 2008.*
Newman and Ihrman; "The Behavior of o-Aroylbenzoic Acid Types in Acidic Media"; *Journal of the American Chemical Society*; (1958); 80: 3652-3656.
Yang and Wong; "Regiospecific Synthesis of 3,4-Disubstituted furans and 3-Substituted furans Using 3-4-Bis(tri-n-butylstannyl)furan an 3-(Tri-n-butylstannyl)furan as Building Blocks"; *Tetrahedron*; (1994): 50(32): 9583-9608.
Koyanagi, et al.; "A Facile Synthesis of 2-Acetylnaphtho[2,3-b]furan-4,9-dione"; *Journal of Heterocyclic Chemistry, Heterocorporation*, Provo, US; (1995); 32(4): 1289-1291.
Alashev, et al.; "Synthesis of macrocyclic compounds 20.2,3-Benzo-5-oxa[10]-alpha-cyclothiene-1,4-dione and products of its reductive desulfurization"; (1977).
International Search Report dated Jun. 25, 2006.

* cited by examiner

*Primary Examiner*—Rebecca L Anderson
*Assistant Examiner*—Shawquia Young
(74) *Attorney, Agent, or Firm*—Sonnenschein Nath & Rosenthal LLP

(57) ABSTRACT

The present invention relates to novel inhibitors of prolyl endopeptidase of formula (1)

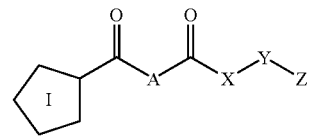

(1)

wherein I, A, X, Y and Z are specified in the description. The compounds are useful for the treatment of diseases such as mild cognitive impairment (MCI), Alzheimer's disease, Down Syndrome, Parkinson disease and Chorea Huntington.

44 Claims, No Drawings

INHIBITORS OF PROLYL ENDOPEPTIDASE

RELATED APPLICATIONS

This application is claims priority under 35 U.S.C. § 119 (e), to U.S. Provisional Application Ser. No. 60/670,165 filed Apr. 11, 2005, the entirety of which is incorporated herein by reference.

FIELD OF THE INVENTION

The invention relates to novel inhibitors of prolyl endopeptidase (PEP, EC 3.4.21.26), in particular to novel diketones as PEP inhibitors.

BACKGROUND OF THE INVENTION

Prolyl endopeptidase (PEP; EC 3.4.21.26; also called prolyl oligopeptidase) is a serine peptidase characterized by oligopeptidase activity. It is the name giving enzyme of family S9A, prolyl oligopeptidases, in clan SC (1). Enzymes belonging to clan SC are distinct from trypsin- or subtilisin-type serine peptidases by structure and by order of the catalytic triad residues in the primary sequence (2;3). The recently reported three dimensional structure of PEP revealed a two domain organization (4). The catalytic domain displays an α/β hydrolase fold in which the catalytic triad (Ser554, His680, Asp641) is covered by a so-called β-propeller domain. Most likely, the propeller domain controls the access of potential substrates to the active site of the enzyme and excludes peptides having more than 30 amino acids.

Despite a profound knowledge of the enzymatic and structural properties of PEP, the biological function of this enzyme is far from being fully understood (5;6). Highly conserved in mammals, PEP is ubiquitously distributed, with high concentrations occurring in the brain (7). Recently, the enzyme gained pharmaceutical interest due to a reported cognitive enhancement induced by treatment with specific PEP inhibitors. In rats displaying scopolamine-induced amnesia, PEP inhibition caused acetylcholine release in the frontal cortex and hippocampus (8). Furthermore, administration of a PEP inhibitor in rats with middle cerebral artery occlusion prolonged passive avoidance latency and reduced the prolonged escape latency in the Morris water maze task (9). The potential of PEP inhibitors as antidementia drugs was further confirmed by reports of neuroprotective effects. Inducing neurodegeneration in cerebellar granule cells led to increased neuronal survival and enhanced neurite outgrowth in presence of a PEP inhibitor (10). Moreover, the level of $m_3$-muscarinic acetylcholine receptor mRNA was found to be increased after PEP inhibition. This resulted in a stimulated phosphoinositide turnover.

It has been hypothesized that these effects are due to modulation of neuropeptide bioactivity by PEP (11). In vitro, PEP is able to rapidly inactivate several neuropetides, including substance P and arginine-vasopressin (AVP) by limited proteolysis (12;13). Neuropeptides, such as substance P or AVP are known to influence learning and memory (14;15). The administration of substance P can induce long-term potentiation (LTP), a well established parameter for learning and memory (16). Binding of substance P to neurokinin 1 receptor stimulates a G-protein mediated increase in $IP_3$ concentration and a release of $Ca^{2+}$ from intracellular stores within the endoplasmic reticulum (ER) (17;18). It is well established, but untested for substance P, that $Ca^{2+}$ release from these stores is implicated in the induction of LTP and in learning and memory (19). In postsynaptic cells, LTP is prevented by the inhibition of $IP_3$ receptors, demonstrating the crucial role of $IP_3$ formation and $Ca^{2+}$ release in this learning and memory model (20). It should be noted, however, that PEP is primarily located in the cytosol (21), whereas the interaction between the neuropeptides and their receptors takes place on the cell surface. Recently, Hasebe et al. found, that cytosolic prolyl endopeptidase is involved in the degradation of p40-phox splice variant protein in myeloid cells (22).

EP 0 172 458 discloses N-phenyl alkanoyl pyrrolidine derivatives useful as anti-amnesic agents.

EP 0 359 547 discloses pyridine compounds inhibiting prolylendo peptidase activity and useful for the treatment of amnesia.

U.S. Pat. No. 5,340,832 discloses N-substituted carbamoyl-alkanoyl-prolinal derivatives useful as inhibitors of prolyl endopeptidase for treating amnesia.

U.S. Pat. No. 5,763,576 discloses tetrapeptide alpha-ketoamides as selective and total inhibitors of serine and cysteine proteases. These compounds are useful in the treatment of tissue damage and various inflammatory conditions, such as blistering, and in the treatment of neurodegenerative diseases such as ischemia, stroke and Alzheimer's disease. The compounds are also inhibitors for blood coagulation enzymes and are useful anticoagulants for the treatment of thrombosis.

WO 91/18891 discloses aromatic pyrrolidine and thiazolidine amide(s) as prolyl endopeptidase inhibitors, which are useful for treating CNS disorders such as various memory or learning dysfunctions associated with disease e.g. Alzheimer's disease; amnesia; dementia; anxiety; ischemia; and damage caused by stroke.

WO 94/12474 discloses cyclic ketone compounds as prolyl endopeptidase inhibitors-including two nitrogen-containing heterocycles linked by a carbonyl group. These compounds inhibit the degradation and deactivation of TRH, substance P, neurotensin and vasopressin. They are useful for the treatment and prevention of amnesia and of dementia including Alzheimer's disease.

WO 95/03277 discloses N-substituted pyrrolidinyl-oxoacetamide compounds as protease (especially PEP) inhibitors useful for treating memory loss e.g. Alzheimer's disease, and auto-immune disorders.

WO 95/15310 discloses prolyl peptide derivatives as prolyl endopeptidase inhibitors. These compounds can be used as memory enhancing agents to improve mental capacity, ability to recall cognitive events, and learned motor activities. Thus the compounds of WO 95/15310 may be used in patients suffering from aphasia, apraxia, agnosia, or any type of amnesias, benign forgetfulness and Korsakoff's syndrome. The compounds may also be used to prevent or slow memory deficits.

WO 97/07116 discloses PEP inhibitors for the use in treatment of acute events (such as ischemia and hypoxia) and progressive neurodegenerative disorders, including Alzheimer's disease, AIDS dementia and Huntington's disease.

WO 98/35960 discloses PEP inhibitors useful as nootropics having memory enhancing and anti-amnesic effects useful in the treatment of age-related cognitive decline and neuroprotectants useful for treatment of acute events (ischemia/hypoxia) and progressive neurodegenerative disorders such as Alzheimer's disease, AIDS related dementia and Huntington's disease.

WO 00/09542 discloses Alpha-keto heterocycles inhibiting the enzymatic activity of a serine proteases. The compounds can be used to inhibit microbial growth, reduce perioperative blood loss, preserve transplantation tissues or organs, inhibit cancer cell growth or tumour progression or tumour metastasis or invasion, treat pulmonary vascular disease, restenosis or pulmonary hypertension myocarditis, bronchopulmonary dysplasia, myocardial necrosis or post-cardiac transplant coronary arteriopathy, atherosclerosis, reperfusion injury, Alzheimer's disease, hypoxia, ischemia and blood coagulation disorders.

REFERENCES

1. Handbook of Proteolytic Enzymes (1998). Barrett, A. J., Rawlings, N. D., and Woessner, J. F. London, Academic Press.
2. Goossens, F., De, M., I, Vanhoof, G., Hendriks, D., Vriend, G., and Scharpe, S. (1995) *Eur. J. Biochem.* 233, 432-441
3. Barrett, A. J. and Rawlings, N. D. (1992) *Biol. Chem. Hoppe Seyler* 373, 353-360
4. Fulop, V., Bocskei, Z., and Polgar, L. (1998) *Cell* 94, 161-170
5. Wetzel, W., Wagner, T., Vogel, D., Demuth, H. U., and Balschun, D. (1997) *Neuropeptides* 31, 41-45
6. Demuth, H. U., Neumann, U., and Barth, A. (1989) *J. Enzyme Inhib.* 2, 239-248
7. Goossens, F., De, M., I, Vanhoof, G., and Scharpe, S. (1996) *Eur. J. Clin. Chem. Clin. Biochem.* 34, 17-22
8. Toide, K., Iwamoto, Y., Fujiwara, T., and Abe, H. (1995) *J. Pharmacol. Exp. Ther.* 274, 1370-1378
9. Shinoda, M., Matsuo, A., and Toide, K. (1996) *Eur. J. Pharmacol.* 305, 31-38
10. Katsube, N., Sunaga, K., Aishita, H., Chuang, D. M., and Ishitani, R. (1999) *J. Pharmacol. Exp. Ther.* 288, 6-13
11. Shishido, Y., Furushiro, M., Tanabe, S., Shibata, S., Hashimoto, S., and Yokokura, T. (1999) *Eur. J. Pharmacol.* 372, 135-142
12. Mentlein, R. (1988) *FEBS Lett.* 234, 251-256
13. Wilk, S. (1983) *Life Sci.* 33, 2149-2157
14. Bennett, G. W., Ballard, T. M., Watson, C. D., and Fone, K. C. (1997) *Exp. Gerontol.* 32, 451-469
15. Huston, J. P. and Hasenohrl, R. U. (1995) *Behav. Brain Res.* 66, 117-127
16. Liu, X. G. and Sandkuhler, J. (1998) *Neuroscience* 86, 1209-1216
17. Abdel-Latif, A. A. (1989) *Life Sci.* 45, 757-786
18. Defea, K., Schmidlin, F., Dery, O., Grady, E. F., and Bunnett, N. W. (2000) *Biochem. Soc. Trans.* 28, 419-426
19. Voronin, L., Byzov, A., Kleschevnikov, A., Kozhemyakin, M., Kuhnt, U., and Volgushev, M. (1995) *Behav. Brain Res.* 66, 45-52
20. Komatsu, Y. (1996) *J. Neurosci.* 16, 6342-6352
21. Kimura, A., Yoshida, I., Takagi, N., and Takahashi, T. (1999) *J. Biol. Chem.* 274, 24047-24053
22. Hasebe, T., Hua, J., Someya, A., Morain, P., Checler, F., and Nagaoka, I. (2001) *J. Leu. Biol.* 69, 963-968
23. Yamaguchi, M., Kamei, K., Koga, T., Akima, M., Kuroki, T., and Ohi, N. (1993) *J Med Chem* 36, 4052-4060

Definitions

The term "PEP-inhibitor" or "prolyl endopeptidase inhibitor" is generally known to a person skilled in the art and means enzyme inhibitors, which inhibit the catalytic activity of prolyl endopeptidase (PEP).

As used herein, the term "pharmaceutically acceptable" embraces both human and veterinary use: for example the term "pharmaceutically acceptable" embraces a veterinarily acceptable compound or a compound acceptable in human medicine and health care.

Throughout the description and the claims the expression "acyl" can denote a $C_{1-10}$ acyl (e.g. alkanoyl) residue, preferably a $C_{1-8}$ acyl (e.g. alkanoyl) residue and especially preferred a $C_{1-4}$ acyl (e.g. alkanoyl) residue; "cycloalkyl" can denote a $C_{3-12}$ cycloalkyl residue, e.g. cyclopropyl, cyclobutyl, cyclopentyl, cyclohexyl and cycloheptyl; and "carbocyclic" can denote a $C_{3-12}$ carbocyclic residue, preferably a $C_4$, $C_5$ or $C_6$ carbocyclic residue. By "carbocylic residue" is meant a non-aromatic ring system (including one or more rings) containing ring carbon atoms typically containing 3-12 ring atoms. Examples include cycloalkyl groups e.g. $C_{3-8}$ cycloalkyl. By "aryl" is meant an aromatic ring system (including one or more rings at least one of which will be aromatic) containing ring carbon atoms and typically containing 6-12 ring atoms. Examples of aryl moieties include monocyclic rings such as phenyl, bicyclic rings such as tetralinyl and naphthyl and tricyclic rings such as fluorenyl. "Heteroaryl" is defined as an aryl residue, wherein 1 to 4 e.g. 1, 2 or 3 ring carbon atoms are replaced by heteroatom selected from N, S or O. Examples of heteroaryl groups include 6 membered rings such as pyridinyl (e.g. 2-pyridinyl), pyridazine and pyrimidinyl, 5-membered rings such as furyl, thienyl, pyrrolyl, imidazolyl, oxazolyl, oxadiazolyl, triazolyl, tetrazolyl, thiazolyl and thiadiazolyl and bi-cyclic rings such as benzofuryl, benzothienyl, benzimidazolyl, quinolinyl, chromanyl, indolyl, isoindolyl and quinazolinyl. "Heterocyclic" is defined as a carbocyclic residue, wherein 1, 2 or 3 ring atoms are replaced by heteroatoms selected from N, S or O. Examples of heterocyclic groups include pyrrolidinyl, piperidinyl, tetrahydrofuryl, tetrahydropyranyl and morpholinyl.

Throughout the description and the claims the expression "alkyl" can denote a $C_{1-10}$ alkyl group, preferably a $C_{1-6}$ alkyl group, especially a $C_{1-4}$ alkyl group; example allyl groups include, methyl, ethyl, propyl(n-propyl, i-propyl), butyl(n-butyl, tert-butyl, sec-butyl), pentyl and hexyl. The expression "alk", for example in the expression "alkoxy", and the expression "alkan", for example in the expression "alkanoyl", are defined as for "alkyl"; the expression "alkenyl" can denote a $C_{2-10}$ alkenyl group, preferably a $C_{2-6}$ alkenyl group, which has at least one double bond at any desired location, for example ethenyl or propenyl; the expression "alkynyl" can denote a $C_{2-10}$ alkynyl group, preferably a $C_{2-6}$ alkynyl group, which has at least one triple bond at any desired location, for example ethynyl or propynyl. Alkyl, alkenyl and alkynyl groups may be branched or unbranched.

Alkyl, alkenyl and alkynyl groups may optionally be substituted by one or more halogen and/or hydroxyl groups. Examples of such substituted alkyl groups include fluoromethyl, trifluoromethyl, chloromethyl, hydroxymethyl groups and their ethyl analogues. Preferably alkyl, alkenyl and alkynyl groups are unsubstituted or are substituted by one or more F atoms, and more preferably are unsubstituted.

Aryl, heteroaryl, carbocyclyl and heterocyclyl groups may optionally be substituted by one or more groups selected from alkyl, alkenyl, alkynyl, cycloalkyl, acyl, alkoxy, thioalkyl, halogen, amino, -aminoalkyl, -amino(alkyl)$_2$, -alkyl-COOH, —CONH$_2$, CONH(alkyl), —CON(alkyl)$_2$, nitro, hydroxyl, oxo, —CN and —SCN.

Example substituted aryl groups include chlorophenyl, nitrophenyl, methoxyphenyl, hydroxymethylphenyl and trifluoromethylphenyl.

Example substituted heteroaryl groups include methylpyridine and N-isoindole-1,3-dione.

Example substituted heterocyclyl groups include N-methylpiperazine.

Example -alkylaryl groups include benyzyl. Example -alkylheteroaryl groups include -methylpyridyl.

Stereoisomers:

All possible stereoisomers of the claimed compounds are included in the present invention. Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Pharmaceutically Acceptable Salts:

In view of the close relationship between the free compounds and the compounds in the form of their salts, whenever a compound is referred to in this context, a corresponding salt is also intended, provided such is possible or appropriate under the circumstances.

The pharmaceutically acceptable salt may take a form in which a basic side chain is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Alternatively it may take the form in which an acidic side chain forms a salt with a metal ion (eg sodium, potassium ions and the like) or other positive ion such as ammonium. All pharmaceutically acceptable acid addition salt forms of the compounds of the present invention are intended to be embraced by the scope of this invention.

Polymorph Crystal Forms:

Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention. The compounds, including their salts, can also be obtained in the form of their hydrates, or include other solvents used for their crystallization.

Prodrugs:

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985 and the patent applications DE 198 28 113, DE 198 28 114, WO 99/67228 and WO 99/67279 which are fully incorporated herein by reference.

As used herein, the term "composition" is intended to encompass a product comprising the claimed compound(s) in the therapeutically effective amounts, as well as any product which results, directly or indirectly, from combinations of the claimed compounds.

SUMMARY OF THE INVENTION

The present invention provides compounds that act as inhibitors of prolyl endopeptidase (PEP, EC 3.4.21.26). Those compounds are represented by the general formula 1.

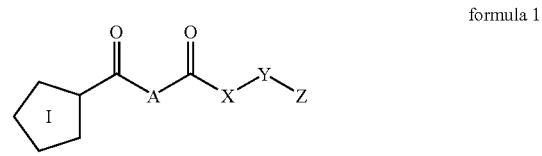

formula 1

DETAILED DESCRIPTION OF THE INVENTION

The present invention provides compounds having the general formula 1 and the pharmaceutically acceptable salts thereof, including all stereoisomers:

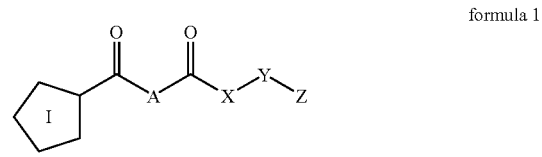

formula 1 wherein

I is furyl or thienyl in either case optionally substituted by one or more groups selected from (i) hydroxyl, nitro, halogen and cyano and (ii) methyl, ethyl, methoxy, and ethoxy wherein one or more hydrogen atoms of said groups is optionally substituted by halogen (e.g. fluorine).

A is selected from a group of formula (I) to (VI):

(I)

(II)

(III)

(IV)

-continued

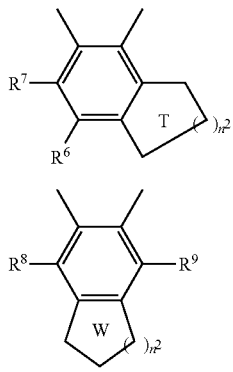

wherein:
$n^1$ is an integer 1-5;
$n^2$ is an integer 1-3;
$R^1$-$R^9$ are independently H, alkyl, alkenyl, alkynyl, carbocycle, aryl, -alkylaryl, heterocycle, heteroaryl or -alkylheteroaryl;
J is $NR^{10}$, S or O, wherein $R^{10}$ is H, alkyl, alkenyl, alkynyl, carbocycle, aryl, -alkylaryl, heterocycle, heteroaryl or -alkylheteroaryl;
or J is $CR^{11}R^{12}$, wherein $R^{11}$ and $R^{12}$ are independently H, alkyl, alkenyl, alkynyl, carbocycle, aryl, alkylaryl, heterocycle, heteroaryl or alkylheteroaryl, or $R^{11}$ and $R^{12}$ can be connected to form a carbocyclic ring with up to 7 members (e.g. a 5- or 6-membered ring);
K is N or $CR^3$, wherein $R^{13}$ is H, alkyl, alkenyl, alkynyl, carbocycle, aryl, -alkylaryl, heterocycle, heteroaryl or -alkylheteroaryl;
L, M, Q, U are independently N or C, provided that when L, M, Q and/or U represents N it may optionally be quaternised by the residues $R^2$-$R^5$ to form a salt or else the corresponding $R^2$, $R^3$, $R^4$ and/or $R^5$ moiety is absent;
T represents a carbocycle, heterocycle, aryl or heteroaryl;
W represents a carbocycle, heterocycle, aryl or heteroaryl;
X is $NR^{14}$ or O, wherein $R^{14}$ is H, alkyl, alkenyl, alkynyl, carbocycle, aryl, -alkylaryl, heterocycle, heteroaryl or -alkylheteroaryl;
Y is alkyl, alkenyl, alkynyl, carbocycle, aryl, heterocycle, heteroaryl or may be absent (i.e. a bond);
Z is alkyl, a carbocycle, aryl, heterocycle or heteroaryl.

When I represents substituted furyl or thienyl, example substituents include methyl, fluoromethyl or chloro. When I is substituted, preferably it is substituted by at most one group. Preferably I represents unsubstituted furyl or thienyl. I may, for example, represent 2-furyl, 3-furyl, 2-thienyl or 3-thienyl. Most preferably I represents thienyl, especially 2-thienyl. In another preferred embodiment I represents 2-furyl.

Examples of carbocycle that Y may represent include $C_3$-$C_5$ cycloalkyl.

Preferably $n^1$ is 3.

Preferably $n^2$ is 2.

Preferably $R^1$ and $R^6$-$R^{14}$ are independently H or Me, especially H.

X is preferably O or NH, particularly O.

Y is preferably absent or represents $CH_2$, $(CH_2)_2$ or $(CH_2)_3$, particularly $CH_2$, $(CH_2)_2$ or $(CH_2)_3$. In one embodiment of the invention Y represents $(CH_2)_2$. In a second embodiment of the invention Y represents $(CH_2)_3$. In a third embodiment of the invention Y represents $CH_2$.

Y may also suitably represent the carbocycle moiety:

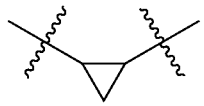

When Z represents alkyl, suitably it represents $C_{2-6}$ alkyl eg n-butyl.

Suitably Z represents a carbocycle, aryl, heterocycle or heteroaryl.

Z is preferably aryl or heteroaryl more preferably phenyl or thienyl, optionally substituted by one or more halogen atoms (e.g. chlorine or alternatively bromine or fluorine) or one or more alkyl groups (e.g. methyl) or nitro. Z is most suitably phenyl, 3-methylphenyl, 4-methylphenyl, 2-chlorophenyl, 3-chlorophenyl, 4-chlorophenyl, thien-2-yl and thien-3-yl. Other example Z groups include 4-nitro-phenyl, 2-indanyl, 2-naphthyl, 9-fluorenyl, 3-methoxyphenyl and 2-benzothienyl. Other example Z groups include 3-trifluoromethylphenyl, 3-nitro-phenyl, 2-bromophenyl, 2-fluorophenyl, 3-fluorophenyl, 4-fluorophenyl, 3-hydroxyphenyl and 2,3-dichlorophenyl. Another example Z group is n-butyl.

K may, for example, represent N or CH.

J may, for example, represent NH or $CH_2$.

Ring T may, for example, represent a carbocycle such as cyclopentyl or cyclohexyl or a heterocycle such as pyrrolidine or piperidine. Ring T together with the benzene ring to which is attached may, for example, represent a 12 membered bicyclic aryl ring such as naphthalene or a 11 or 12 membered bicyclic heteroaryl ring such as indoline, isoindoline, indole, 3H-indole, chroman, isoindole, quinoline or isoquinoline. Preferably T is a 6-membered ring.

Ring W may, for example, represent a carbocycle such as cyclopentyl or cyclohexyl or a heterocycle such as pyrrolidine or piperidine. Ring T together with the benzene ring to which is attached may, for example, represent a 12 membered bicyclic aryl ring such as naphthalene, or a 11 or 12 membered bicyclic heteroaryl ring such as indoline, isoindoline, indole, 3H-indole, chroman, isoindole, quinoline or isoquinoline. In one preferred embodiment W is a 5-membered ring. In another embodiment of the invention W is a 6-membered ring.

Preferably L-$R^2$ represents CH, CMe or N, especially CH.
Preferably M-$R^3$ represents CH, CMe or N, especially CH.
Preferably Q-$R^4$ represents CH, CMe or N, especially CH.
Preferably U-$R^5$ represents CH, CMe or N, especially CH.

Suitably A represents a group of formula (II), (III), (IV), (V) or (VI) eg a group of formula (II), (III) or (IV).

Preferably A represents a group of formula (II) (e.g. where $n^2$ is 2) or (IV) especially a group of formula (IV), more especially A represents phenyl (i.e. $R^2$, $R^3$, $R^4$ and $R^5$ are H and L, M Q and U are C). When A represents a group of formula (II) preferably the two groups attached have trans orientation.

A process for preparing compounds of formula (1) comprises reacting a compound of formula (IA)

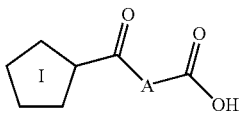

Formula (IA)

or an activated derivative thereof, with a compound of formula (IB):

     Formula (IB)

The compounds of formula (IA) may be reacted as acid with the compound of formula (IB) in an inert polar solvent in the presence of concentrated sulphuric acid with heating to give an ester (i.e. X represents O). For the amides (i.e. X represents $NR^{14}$), compounds of formula (IA) may suitably be activated to give the a mixed anhydride, and to that the compound of formula (IB) may be added.

When A represents a group of formula (II), (III), (IV), (V) or (VI), certain compounds of formula (IA) may be prepared by reacting a compound of formula (IC)

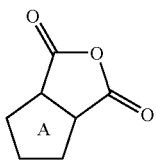

Formula (IC)

in which ring A represents a group of formula (II), (III), (IV), (V) or (VI), with a compound of formula (ID):

     Formula (ID)

This reaction may be performed under Friedel-Crafts acylation conditions i.e. in the presence of $AlCl_3$ to generate the 2-substituted compounds of formula (IA). The specifics of this reaction will be well known to a person skilled in the art or may, for example, be gleaned by reference to March J "Advanced Organic Chemistry" Third Ed (1985) published J Wiley and Sons or (23).

To generate the 3-substituted compounds of formula (IA), the 3-iodothiophene or the 3-bromofuran (or substituted derivative of either) respectively are treated with t-BuLi at −78° C. to obtain an organo-metal-intermediate. This intermediate may be reacted with a cyano-compound given in formula (IE):

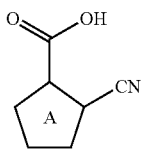     Formula (IE)

A detailed description for the procedure is disclosed in the patent U.S. Pat. No. 3,408,358, which is specifically incorporated herein in its entirety.

When A represents a group of formula (I), compounds of formula (IA) may be prepared by reacting a compound of formula (IF) under Friedel-Crafts acylation conditions as mentioned above. After purification, compounds of formula (IA) may be modified to yield compounds of formula (1) by the same procedures as described for formula (IA) above:

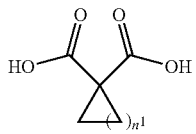     Formula (IF)

Compounds of formula (IA), (IB), (IC), (ID), (IE) and (IF) are either known or may be prepared by conventional methods known per se.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using conventional methods known from the art.

Compounds of formula (I) and salts thereof can, if desired, be converted into other salts thereof for example pharmaceutically acceptable salts by conventional means.

In a first aspect of the invention there is provided the compounds of formula (1) for use as a medicament.

The compounds of the present invention may be effective to modulate the basal level of interleukin-6 (IL-6) in human glial cells. Certain compounds show a significant suppression of IL-6 secretion.

IL-6, a pleiotropic cytokine, contributes to a multitude of neuropathological and pathophysiological processes, especially in inflammation, cancer, infection and autoimmune diseases. Overexpression of IL-6 has been implicated in the pathology of multiple myeloma, solid tumors, prostatic cancers, bladder cancers, neurological cancers, Castleman's disease, inflammation, myocardial infarction, Paget's disease, ischemia, asthma, rheumatoid arthritis, psoriasis, Alzheimer's disease, multiple sclerosis, meningitis, stroke, osteoporosis, insulin resistance, obesity, impaired glucose tolerance, type 2 diabetes, cancer-related anorexia and cachexia as well as multidrug resistance. Therefore, reduction of pathological IL-6 concentrations by compounds which are described here may be useful in treatment of IL-6 related diseases, for instance those mentioned above.

With regard to the IL-6 suppressing effect, compounds of formula (1) are preferred, wherein I is furyl or thienyl;

A is phenyl (i.e. $R^2, R^3, R^4$ and $R^5$ are H and L, M Q and U are C);

X is O or NH;

Y is alkyl or $C_3$-$C_5$ cycloalkyl;

Z is 9-fluorene, phenyl, 3-methylphenyl, 4-methylphenyl, 2-thienyl, 3-thienyl, 2-chlorophenyl, 3-chlorophenyl, 4-chlorophenyl, 2,3-dichlorophenyl, 3-methoxyphenyl, 2-fluorophenyl, 3-fluorophenyl, 4-fluorophenyl, 2-bromophenyl or 3-hydroxyphenyl.

More preferably, I is 2-furyl or 2-thienyl, particularly 2-thienyl.

More preferably, Y is $CH_2$, $CH_2CH_2$, $CH_2CH_2CH_2$ or

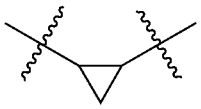

particularly $CH_2CH_2$.

More preferably, Z is phenyl, 4-methylphenyl, 3-thienyl, 2,3-dichlorophenyl, 4-fluorophenyl or 3-hydroxyphenyl, particularly phenyl.

More preferably X is O.

Furthermore, the compounds of the present invention may be effective to modulate the basal level of β-amyloid peptides, especially of $A\beta_{1-40}$ and $A\beta_{1-42}$ in different human cell lines, e.g. neuronal cells. Certain compounds of the present invention show a significant increase of the secretion of β-amyloid peptides.

β-amyloid peptides are considered to be the cause of neurodegeneration and neuronal cell death in patients faced with MCI (Mild Cognitive Impairment) Alzheimer's disease (AD) and for the progression of MCI to AD. Recently, it was shown that the β-amyloid species, which are involved in the onset of MCI and AD, are formed intracellularly. Moreover, not the full-length peptides $A\beta_{1-40}$ and $A\beta_{1-42}$ but N-terminally truncated and N-terminally modified forms of β-amyloid peptides, e.g. $A\beta_{3-40}$, $A\beta_{3-42}$, pGlu-$A\beta_{3-40}$, pGlu-$A\beta_{3-42}$, $A\beta_{11-42}$ and pGlu-$A\beta_{11-42}$ are discussed as the toxic forms (Piccini et al., J. Biol. Chem. 280 (40), 2005, pp. 34186-34192).

The compounds of the present invention may therefore be useful to prevent the formation of neurotoxic β-amyloid peptides, e.g. $A\beta_{3-40}$, $A\beta_{3-42}$, pGlu-$A\beta_{3-40}$, pGlu-$A\beta_{3-42}$, $A\beta_{1-42}$ and pGlu-$A\beta_{11-42}$ by enhancement of the secretion of full-length $A\beta_{1-40}$ and $A\beta_{1-42}$ before N-terminal truncation and modification.

With regard to the increasing effect of the β-amyloid peptide secretion, compounds of formula (1) are preferred, wherein
I is furyl or thienyl;
A is phenyl (i.e. $R^2$, $R^3$, $R^4$ and $R^5$ are H and L, M Q and U are C);
X is O or NH;
Y is alkyl or absent;
Z is 9-fluorene, 2-indanyl, phenyl, 3-methylphenyl, 4-methylphenyl, 2-thienyl, 3-thienyl, 2-chlorophenyl, 3-chlorophenyl, 4-chlorophenyl, 2-nitrophenyl, 3-nitrophenyl or 2-benzothienyl.

More preferably, I is 2-furyl or 2-thienyl, particularly 2-thienyl.

More preferably, Y is $CH_2$, $CH_2CH_2$, or $CH_2CH_2CH_2$, particularly $CH_2$ or $CH_2CH_2$.

More preferably, Z is 9-fluorene, 2-indanyl, phenyl, 3-methylphenyl, 2-thienyl, 3-thienyl, 2-chlorophenyl or 2-nitrophenyl, particularly phenyl.

More preferably X is O.

Furthermore, the present invention provides the use of inhibitors of PEP of the formula 1 for the preparation of a medicament for the treatment of a disease selected from the group consisting of neuroinflammation, Alzheimer's disease, Down Syndrome, Parkinson disease, Chorea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction, dementia, aphasia, apraxia, agnosia, or any type of amnesias, mild cognitive impairment (MCI), benign forgetfulness and Korsakoff's syndrome, pulmonary vascular disease, restenosis or pulmonary hypertension myocarditis, bronchopulmonary dysplasia, myocardial necrosis or post-cardiac transplant coronary arteriopathy, atherosclerosis, reperfusion injury, hypoxia, ischemia and blood coagulation disorders.

The present invention also provides inhibitors of PEP of the formula 1 for use in the treatment of a disease selected from the group consisting of neuroinflammation, Alzheimer's disease, Down Syndrome, Parkinson disease, Chorea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction, dementia, aphasia, apraxia, agnosia, or any type of amnesias, mild cognitive impairment (MCI), benign forgetfulness and Korsakoff's syndrome, pulmonary vascular disease, restenosis or pulmonary hypertension myocarditis, bronchopulmonary dysplasia, myocardial necrosis or post-cardiac transplant coronary arteriopathy, atherosclerosis, reperfusion injury, hypoxia, ischemia and blood coagulation disorders, The present invention also provides a method of treatment for a disease selected from the group consisting of neuroinflammation, Alzheimer's disease, Down Syndrome, Parkinson disease, Chorea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction, dementia, aphasia, apraxia, agnosia, or any type of amnesias, mild cognitive impairment (MCI), benign forgetfulness and Korsakoff's syndrome, pulmonary vascular disease, restenosis or pulmonary hypertension myocarditis, bronchopulmonary dysplasia, myocardial necrosis or post-cardiac transplant coronary arteriopathy, atherosclerosis, reperfusion injury, hypoxia, ischemia and blood coagulation disorders, comprising the administration of a therapeutically active amount of at least one compound of formula 1 to a mammal, preferably a human.

Most preferably, the present invention provides a method of treatment and corresponding uses for a disease selected from the group consisting of mild cognitive impairment (MCI), Alzheimer's disease, Down Syndrome, Parkinson disease and Chorea Huntington, comprising the administration of a therapeutically active amount of at least one compound of formula 1 to a mammal, preferably a human.

In a further embodiment, the compounds of formula 1 are useful to inhibit microbial growth, reduce perioperative blood loss, preserve transplantation tissues or organs, inhibit cancer cell growth or tumour progression or tumour metastasis or invasion.

Combinations

In a further embodiment, the present invention provides a composition, preferably a pharmaceutical composition comprising at least one compound of formula 1 optionally in combination with at least one compound selected from the group consisting of inhibitors of glutaminyl cyclase (QC), LiCl, inhibitors of dipeptidyl aminopeptidases, preferably inhibitors of DP IV or DP IV-like enzymes, NPY-receptor ligands, NPY agonists, acetylcholinesterase (AChE) inhibitors, protein isoaspartate carboxymethyl transferase (PIMT) enhancers, inhibitors of beta secretases, inhibitors of gamma secretases, inhibitors of neutral endopeptidase, inhibitors of Phosphodiesterase-4 (PDE-4), monoamine oxidase (MAO) inhibitors, TNFalpha inhibitors, amyloid protein or amyloid peptide deposition inhibitors, sigma-1 receptor inhibitors and histamine H3 antagonists.

These combinations provide a particularly beneficial effect on behavioral conditions and such combinations are therefore shown to be effective and useful for the treatment of a disease selected from the group consisting of neuroinflammation, Alzheimer's disease, Down Syndrome, Parkinson disease, Chorea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction, dementia, aphasia, apraxia, agnosia, or any type of amnesias, mild cognitive impairment (MCI), benign forgetfulness and Korsakoff's syndrome, pulmonary vascular disease, restenosis or pulmonary hypertension myocarditis, bronchopulmonary dysplasia, myocardial necrosis or post-cardiac transplant coronary arteriopathy, atherosclerosis, reperfusion injury, hypoxia, ischemia and blood coagulation disorders.

The combinations of the present invention are further useful to inhibit microbial growth, reduce perioperative blood loss, preserve transplantation tissues or organs, inhibit cancer cell growth or tumour progression or tumour metastasis or invasion.

Pharmaceutical Compositions

The invention provides pharmaceutical compositions containing at least one compound of formula 1 optionally in combination with at least one agent as mentioned for the combinations above, together with one or more therapeutically acceptable diluents or carriers. The active ingredient(s) is intimately admixed with a pharmaceutical diluent or carrier according to conventional pharmaceutical compounding techniques, which diluent or carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenteral administration, the carrier will usually comprise sterile water, though other ingredients, for example, for purposes such as aiding solubility or for preservation, may be included.

Soluble polymers as targetable drug carriers can include polyvinylpyrrolidone, pyran copolymer, polyhydroxypropylmethacrylamidephenol, polyhydroxyethylaspartamide-phenol, or polyethyleneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like.

Disintegrators include, without limitation, starch, methyl cellulose, agar, bentonite, xanthan gum and the like.

Injectable suspensions may also prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient(s) necessary to deliver an effective dose as described above. The pharmaceutical compositions herein will contain, per dosage unit, e.g., tablet, capsule, powder, injection, suppository, teaspoonful and the like, from about 0.03 mg to 100 mg/kg (preferred 0.1-30 mg/kg) and may be given at a dosage of from about 0.1-300 mg/kg per day (preferred 1-50 mg/kg per day) of each active ingredient or combination thereof. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of each active ingredient or combinations thereof of the present invention.

The tablets or pills of the compositions of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

This liquid forms in which the compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinylpyrrolidone or gelatin.

Where the processes for the preparation of the compounds of the present invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also resolved by formation of diastereomeric esters or amides, followed by chromatographic separation and removal of the chiral auxiliary. Alternatively, the compounds may be resolved using a chiral HPLC column.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitable flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compounds or combinations of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds or combinations of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamid-ephenol, or polyethyl eneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds or combinations of this invention may be administered in any of the foregoing compositions and according to dosage regimens established in the art whenever treatment of the addressed disorders is required.

The daily dosage of the products may be varied over a wide range from 0.01 to 1.000 mg per mammal per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of each active ingredient or combinations thereof for the symptomatic adjustment of the dosage to the patient to be treated. An effective amount of the drug is ordinarily supplied at a dosage level of from about 0.1 mg/kg to about 300 mg/kg of body weight per day. Preferably, the range is from about 1 to about 50 mg/kg of body weight per day. The compounds or combinations may be administered on a regimen of 1 to 4 times per day.

Optimal dosages to be administered may be readily determined by those skilled in the art, and will vary with the particular compound used, the mode of administration, the strength of the preparation, the mode of administration, and the advancement of disease condition. In addition, factors associated with the particular patient being treated, including patient age, weight, diet and time of administration, will result in the need to adjust dosages.

Suitably, in the case of combinations according to the invention, the particularly beneficial effect provided by the treatment of the invention is an improved therapeutic ratio for the combination of the invention relative to the therapeutic ratio for one compound of the combination when used alone and at a dose providing an equivalent efficacy to the combination of the invention.

In a preferred aspect, the particularly beneficial effect provided by the treatment of the invention is indicated to be a synergistic effect relative to the control expected from the effects of the individual active agents.

In a further aspect of the invention, combining doses of at least one compound of formula 1 with at least one agent as defined for the combinations herein will produce a greater beneficial effect than can be achieved for either agent alone at a dose twice that used for that agent in the combination.

In a preferred aspect, the dosage level of each of the active agents when used in accordance with the treatment of the invention will be less than would have been required from a purely additive effect upon the neuronal condition.

Without being limited by theory, it is also considered that the treatment of the invention will effect an improvement, relative to the individual agents, in decreasing the intracellular deposition of pGlu-amyloid-beta-peptides and thereby dramatically slowing down the plaque formation in the brain of a mammal, preferably in human brain.

In a further aspect, the invention also provides a process for preparing a pharmaceutical composition comprising at least one at least one compound of formula 1 optionally in combination with at least one agent as defined for the combinations herein and a pharmaceutically acceptable carrier therefor, which process comprises admixing the compound of formula 1 and said optional agent(s) and a pharmaceutically acceptable diluent or carrier.

The compositions are preferably in a unit dosage form in an amount appropriate for the relevant daily dosage.

Suitable dosages, including especially unit dosages, of the compounds of formula 1, QC-inhibitors, LiCl, inhibitors of dipeptidyl aminopeptidases, preferably inhibitors of DP IV or DP IV-like enzymes, NPY-receptor ligands, NPY agonists, acetylcholinesterase (AChE) inhibitors, PIMT enhancers, inhibitors of beta secretases, inhibitors of gamma secretases, inhibitors of neutral endopeptidase, inhibitors of Phosphodiesterase-4 (PDE-4), monoamine oxidase (MAO) inhibitors, TNFalpha inhibitors, amyloid protein or amyloid peptide deposition inhibitors, sigma-1 receptor inhibitors and histamine H3 antagonists include the known dosages including unit doses for these compounds as described or referred to in reference text such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) or the above mentioned publications.

Preferred compounds of formula I are those having an $IC_{50}$ value or a $K_i$ value, and preferably an $IC_{50}$ value and a $K_i$ value, of less than $1\times10^{-6}$, in particular less than $1\times10^{-7}$ and especially less than $1\times10^{-8}$ M.

Preferred compounds of formula I have a molecular weight of less than 2000 Da especially less than 1000 Da particularly less than 600 Da, e.g. less than 500 Da.

Compounds and combinations of the invention may have the advantage that they are, for example, more potent, more selective, have fewer side-effects, have better formulation and stability properties, have better pharmacokinetic properties, be more bioavailable, be able to cross blood brain barrier and are more effective in the brain of mammals, are more compatible or effective in combination with other drugs or be more readily synthesized than other compounds of the prior art.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications mentioned above are herein incorporated in their entirety by reference.

The invention embraces all combinations of preferred and more preferred groups and embodiments of groups recited above.

EXAMPLES

Biological Evaluation, Determination of $IC_{50}$- and $K_i$-Values of PEP-Inhibitors Recombinant human prolyl oligopeptidase was used for measurement. Recombinant expression was performed in *E. coli* under standard conditions as described elsewhere in the state of the art.

For activity measurements the chromogenic substrate Z-Gly-Pro-pNA was used in HEPES buffer pH 7.6 containing 50 mM HEPES, 200 mM NaCl, 1 mM EDTA, 1 mM DTT, 0.006% Brij35. Measurements were carried out at 30° C. Release of pNA were monitored continuously at 405 nm.

$IC_{50}$ values were determined using one substrate concentration (0.15 mM) and 11-15 serial dilutions of inhibitor starting with 0.1 mM. $IC_{50}$ values were calculated using non-linear regression to a 4-parameter equation (Prism 4.0, GraphPad).

For Ki determination 4 substrate (0.15 mM, 0.08 mM 0.04 mM, 0.02 mM) and 7 inhibitor concentrations in an appropriate range were used. Calculations were performed by multiple non-linear regression analysis to the equation for competitive inhibition using GraFit 5.0 Software (Erithacus Software).

IL-6 ELISA

To analyze basal secretion of IL-6, human glial U-343 cells were cultured in 6 well plates ($1.5\times10^6$ cells/well, Greiner) and treated with specific PEP inhibitors as indicated (20 μM each) for 24 hours in serum-free D-MEM medium (invitrogen). Aliquots of 40 μl conditioned medium were used to quantify the amount of secreted IL-6 by an human-specific IL-6 ELISA (Biosource) following the manufacturer's instructions. All data were obtained in quadruplicate. For the calculation of the IL-6 concentration in the cell culture medium after PEP-inhibitor treatment, the basal IL-6 concentration of the cell culture medium of untreated cell samples was set to 100%. The results of the measurement of the IL-6 concentration with PEP-inhibitor treated cells are presented as % of the untreated cell samples.

β-Amyloid ELISA

Cell Culture.

The human glioma cell line, U-343 and the human neuroblastoma cell line, SH-SY5Y were maintained in Dulbecco's modified Eagle's medium (DMEM) containing 10% fetal bovine serum (Gibco BRL, Karlsruhe, Germany) and incubated at 37° C. in a 5% $CO_2$ atmosphere. Culture media contained in general 60 μg/ml gentamycin (Gibco BRL, Karlsruhe, Germany).

Metabolic Labeling.

For the metabolic labeling approach, $5\times10^5$ cells were seeded in 35 mm culture dishes and then grown for 40 hours in the appropriate culture media. After washing, cells were incubated with [$^{35}$S]methionine (1 μCi/ml, ICN Biomedicals, Eschwege, Germany) in DMEM without L-methionine, L-cysteine and L-cystine (ICN Biochemicals) for 2 hours, followed by a 24-h chase with/without the PEP inhibitor Fmoc-Ala-Pyrr-CN (5 μM) at 37° C. in serum-free culture medium. The radiolabeled proteins in the chase medium were precipitated with 8% (w/v) TCA-solution and centrifuged at 15500×g for 10 min. After washing, the protein pellets were resuspended in 1 ml of distilled water and the radioactivity was measured in a Tri-carb2100TR-scintillation counter (Packard, Dreieich, Germany). All measurements were carried out at least in quadruplicate, and the experiment was repeated four times.

β-Amyloid ELISA.

To quantify intracellular and extracellular concentrations of 0-amyloid peptides, 1-40 and 1-42, U-343 and SH-SY5Y cells were cultured in 6 well plates ($1.5 \times 10^6$ cells/well) and treated with specific PEP inhibitors (20 µM each) for 24 hours. For quantitation of secreted β-amyloid peptides the conditioned medium was collected and concentrated by lyophylisation. Likewise, after determination of the cell numbers/well (casy cell counter I, Schärfe System, Reutlingen, Germany), cells were lyzed with cell extraction buffer (Biosource, Solingen, Germany) according to the manufacturer's protocol. The protein concentration was determined by the method of Bradford (1976). Aliquots of 100 µl were used to quantify β-amyloid peptides 1-40 and 1-42 in quadruplicate by ELISA (IBL, Hamburg, Germany) following the manufacturer's instructions. All obtained intracellular and extracellular concentrations were normalized to cell numbers and protein concentration, respectively.

For the calculation of the concentration of β-amyloid peptides 1-40 and 1-42 in the cell culture medium after PEP-inhibitor treatment, the basal concentration of β-amyloid peptides 1-40 and 1-42 in the cell culture medium of untreated cell samples was set to 100%. The results of the measurement of the concentration of β-amyloid peptides 1-40 and 1-42 with PEP-inhibitor treated cells are presented as % of the untreated cell samples.

The preferred PEP inhibitors of the present invention show a significant reduction of the IL-6 level and an increased β-amyloid secretion, especially of β-amyloid peptides 1-40 and 1-42.

Example Compounds

| Example | Structure | $M_r$ (g/mol) | ESI-MS $(M + H^+)$ | $IC_{50}$ (M) | $K_i$ (M) | Gradient and time of retention for HPLC[a] | Extracellular IL-6 concentration[b], % of untreated cells | Extracellular Aβ-concentration, % of control |
|---|---|---|---|---|---|---|---|---|
| 1 | 2-(thiophene-2-carbonyl)benzoic acid benzyl ester | 322.4 | 323.3 | $7.23 * 10E{-}7$ | $1.04 * 10E{-}7$ | A: 21.60' | 92.6 | 197.2 |
| 2 | 2-(thiophene-2-carbonyl)benzoic acid phenethyl ester | 336.4 | 337.2 | $7.82 * 10E{-}8$ | $2.59 * 10E{-}8$ | A: 23.95' | 65.5 | 213.9 |
| 3 | 2-(thiophene-2-carbonyl)benzoic acid 4-nitrobenzyl ester | 367.4 | 368.1 | $2.37 * 10E{-}7$ | $1.33 * 10E{-}7$ | A: 20.10' | 244.9 | 140.9 |
| 4 | 2-(thiophene-2-carbonyl)benzoic acid 9H-fluoren-9-ylmethyl ester | 410.5 | 411.3 | $1.33 * 10E{-}7$ | $5.85 * 10E{-}8$ | A: 25.20' | 40.7 | 200 |

-continued
| Example | Structure | $M_r$ (g/mol) | ESI-MS (M + H⁺) | IC$_{50}$ (M) | K$_i$ (M) | Gradient and time of retention for HPLC[a] | Extra-cellular IL-6 concentration[b], % of untreated cells | Extra-cellular Aβ-concentration, % of control |
|---|---|---|---|---|---|---|---|---|
| 5 | 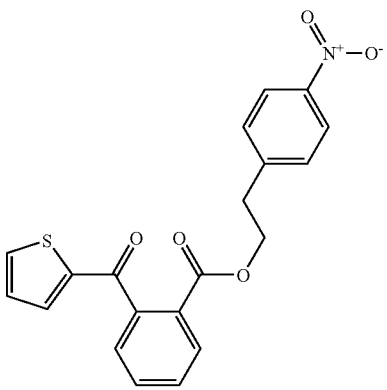 | 381.4 | 382.2 | 1.62 * 10E−7 | 1.32 * 10E−7 | A: 20.67' | 101.5 | 160.1 |
| 6 | 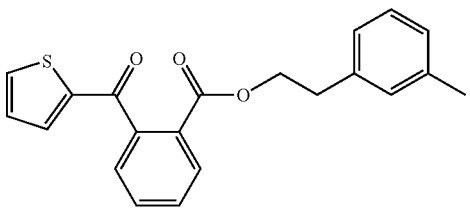 | 350.4 | 351.4 | 1.52 * 10E−7 | 7.40 * 10E−8 | A: 23.34' | 45.8 | 215.2 |
| 7 | 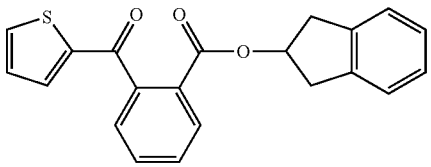 | 384.4 | 349.3 | 1.30 * 10E−7 | 8.44 * 10E−8 | A: 21.95' | 85.3 | 204.9 |
| 8 | 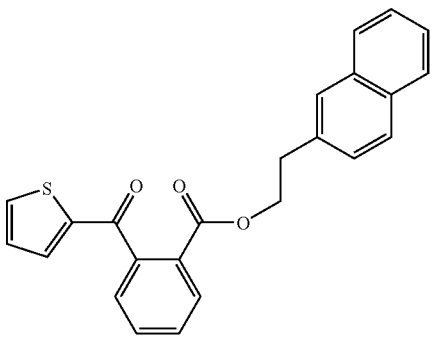 | 386.5 | 387.3 | 2.59 * 10E−7 | 1.13 * 10E−7 | A: 24.47' | 93.7 | 165 |
| 9 | 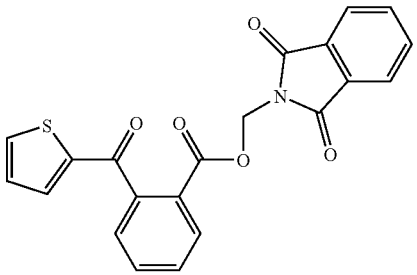 | 381.4 | 392.2 | n.i. | n.m. | A: 16.64' | 124.3 | 113.3 |

-continued

| Example | Structure | $M_r$ (g/mol) | ESI-MS (M + H⁺) | IC$_{50}$ (M) | $K_i$ (M) | Gradient and time of retention for HPLC[a] | Extra-cellular IL-6 concentration[b], % of untreated cells | Extra-cellular Aβ-concentration, % of control |
|---|---|---|---|---|---|---|---|---|
| 10 | 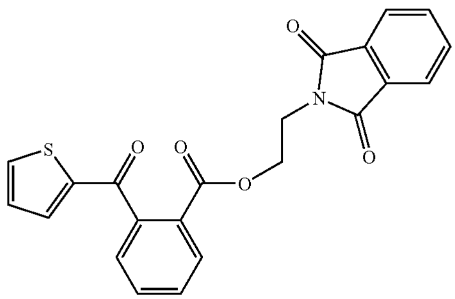 | 405.4 | 406.4 | 7.53 * 10E−7 | 5.24 * 10E−7 | A: 17.27' | 142.6 | 125.2 |
| 11 | 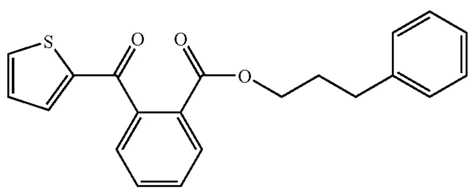 | 350.4 | 351.4 | 3.49 * 10E−7 | 1.99 * 10E−7 | A: 23.13' | 42.4 | 192.2 |
| 12 | 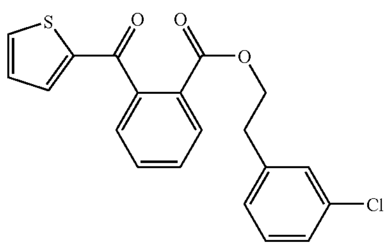 | 370.8 | 371.2 | 1.61 * 10E−7 | 4.66 * 10E−7 | A: 23.36' | 53.7 | 191.1 |
| 13 | 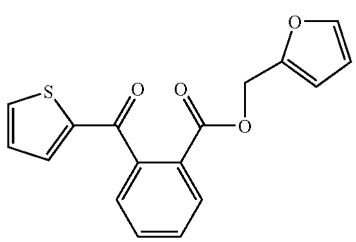 | 312.3 | 313.2 | 1.12 * 10E−6 | n.m. | A: 16.56' | 74.2 | 121.9 |
| 14 | 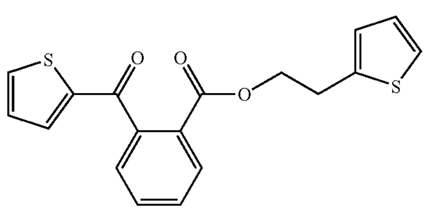 | 342.4 | 343.0 | 9.33 * 10E−8 | 7.75 * 10E−8 | A: 20.89' | 41.4 | 200 |
| 15 | 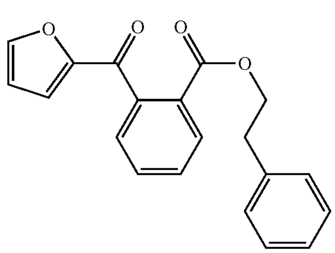 | 320.3 | 321.3 | 1.70 * 10E−8 | 7.56 * 10E−8 | A: 19.55' | 48.2 | 144 |

-continued

| Example | Structure | $M_r$ (g/mol) | ESI-MS (M + H⁺) | IC$_{50}$ (M) | K$_i$ (M) | Gradient and time of retention for HPLC[a] | Extra-cellular IL-6 concentration[b], % of untreated cells | Extra-cellular Aβ-concentration, % of control |
|---|---|---|---|---|---|---|---|---|
| 16 | 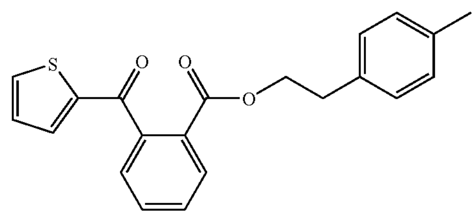 | 350.4 | 351.3 | 3.81 * 10E−8 | 1.68 * 10E−8 | A: 21.73' | 26.7 | 180.4 |
| 17 | 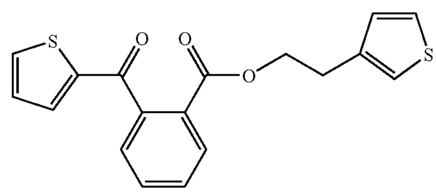 | 342.4 | 343.0 | 9.65 * 10E−8 | 7.60 * 10E−9 | B: 23.09' | 26.5 | 236.9 |
| 18 | 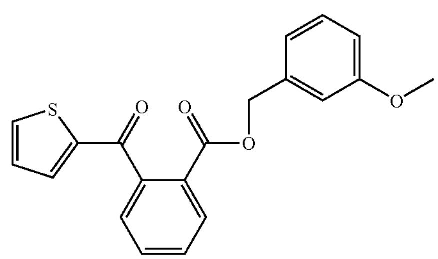 | 352.4 | 353.3 | n.i. | n.m. | A: 22.19' | 63.3 | 105.8 |
| 19 | 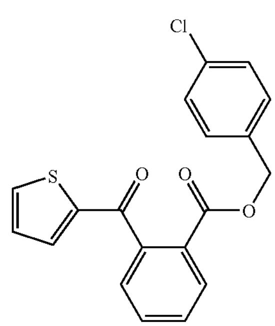 | 356.8 | 357.2 | 2.43 * 10E−7 | 3.27 * 10E−8 | A: 20.99' | 35.2 | 195 |
| 20 | 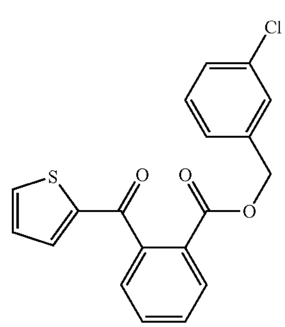 | 356.8 | 357.2 | 7.89 * 10E−7 | 4.20 * 10E−8 | A: 20.77' | 49.2 | 180.1 |

-continued

| Example | Structure | $M_r$ (g/mol) | ESI-MS $(M + H^+)$ | $IC_{50}$ (M) | $K_i$ (M) | Gradient and time of retention for HPLC[a] | Extra-cellular IL-6 concentration[b], % of untreated cells | Extra-cellular Aβ-concentration, % of control |
|---|---|---|---|---|---|---|---|---|
| 21 | 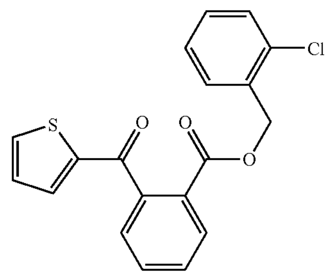 | 356.8 | 357.1 | 2.72 * 10E−7 | 5.17 * 10E−8 | A: 20.48' | 62.1 | 219.6 |
| 22 | 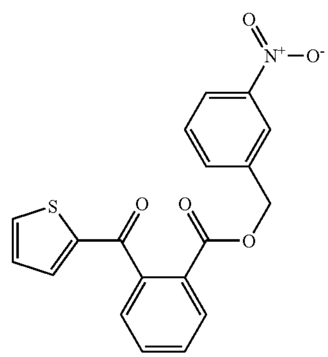 | 367.4 | 368.1 | 7.63 * 10E−9 | 4.47 * 10E−8 | A: 18.16' | 102.6 | 153 |
| 23 | 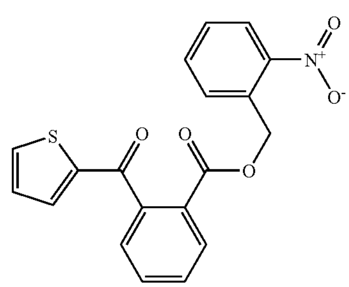 | 367.4 | 368.1 | 8.31 * 10E−7 | 1.41 * 10E−7 | A: 18.05' | 109.0 | 240 |
| 24 | 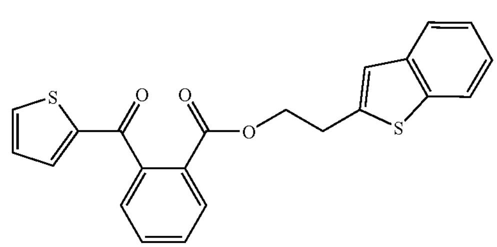 | 392.5 | 393.2 | 4.05 * 10E−8 | 2.11 * 10E−8 | A: 22.48' | 66.9 | 165.4 |
| 25 | 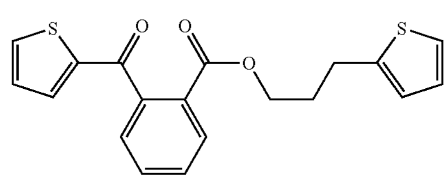 | 356.5 | 357.2 | 3.20 * 10E−7 | 3.96 * 10E−8 | A: 20.77' | 69.0 | 196.7 |

-continued

| Example | Structure | $M_r$ (g/mol) | ESI-MS (M + H$^+$) | IC$_{50}$ (M) | K$_i$ (M) | Gradient and time of retention for HPLC$^a$ | Extra-cellular IL-6 concentration$^b$, % of untreated cells | Extra-cellular Aβ-concentration, % of control |
|---|---|---|---|---|---|---|---|---|
| 26 | 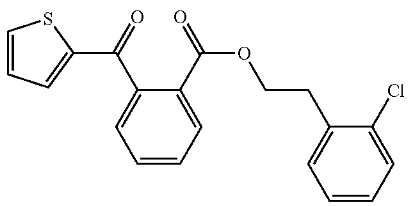 | 370.8 | 371.1 | 6.10 * 10E−7 | n.m. | A: 21.68' | 36.6 | 206.6 |
| 27 | 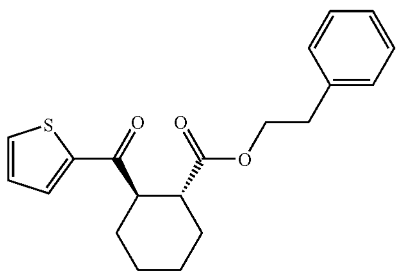 | 342.4 | 343.2 | 4.23 * 10E−8 | 5.24 * 10E−8 | A: 22.29' | 19.6 | 298.3 |
| 28 | 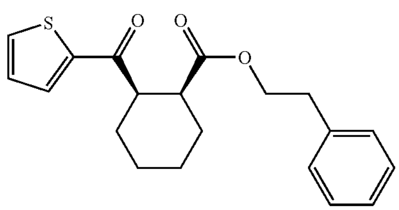 | 342.4 | 343.2 | 7.23 * 10E−8 | 4.81 * 10E−8 | A: 23.95' | 78.8 | n.m. |
| 29 | 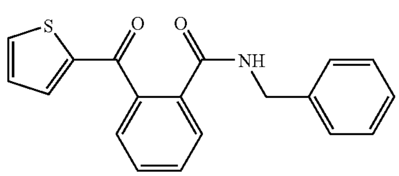 | 321.4 | 322.1 | 7.47 * 10E−6 | n.m. | A: 16.49' | 120.9 | 109.3 |
| 30 | 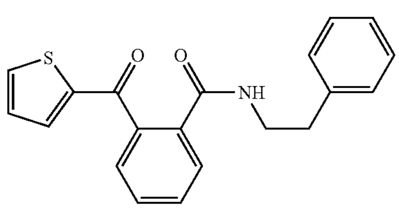 | 335.4 | 336.3 | 6.83 * 10E−7 | 2.56 * 10E−7 | A: 20.14' | 42.3 | 204.8 |
| 31 | 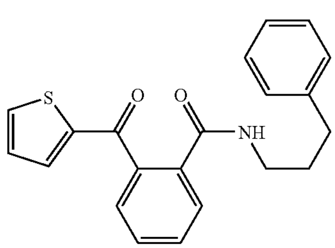 | 349.4 | 350.4 | 1.04 * 10E−5 | 2.90 * 10E−6 | A: 19.03' | 30.0 | 203 |

-continued

| Example | Structure | M$_r$ (g/mol) | ESI-MS (M + H$^+$) | IC$_{50}$ (M) | K$_i$ (M) | Gradient and time of retention for HPLC$^a$ | Extra-cellular IL-6 concentration$^b$, % of untreated cells | Extra-cellular Aβ-concentration, % of control |
|---|---|---|---|---|---|---|---|---|
| 32 | 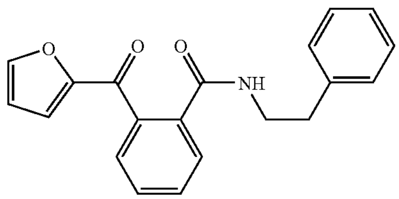 | 319.4 | 320.2 | 1.09 * 10E−5 | n.m. | A: 20.40' | 32.0 | 63.9 |
| 33 | 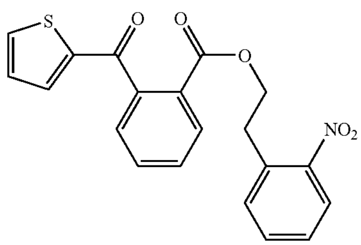 | 381.4 | 382.2 | 2.11 * 10E−7 | 1.10 * 10E−8 | A: 18.77' | 54.5 | n.m. |
| 34 | 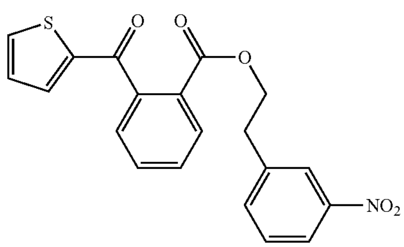 | 384.4 | 382.2 | 1.72 * 10E−7 | 5.76 * 10E−8 | A: 18.80' | 78.8 | n.m. |
| 35 | 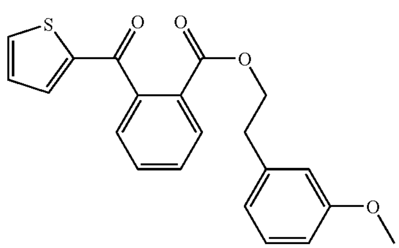 | 366.4 | 367.2 | 1.11 * 10E−7 | 7.91 * 10E−8 | A: 19.55' | 46.7 | n.m. |
| 36 | 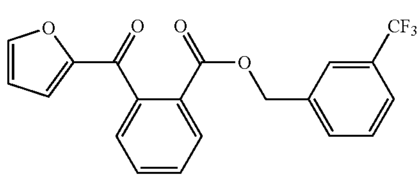 | 390.4 | 391.2 | 1.20 * 10E−6 | 5.94 * 10E−7 | A: 21.17' | 79.8 | n.m. |
| 37 | 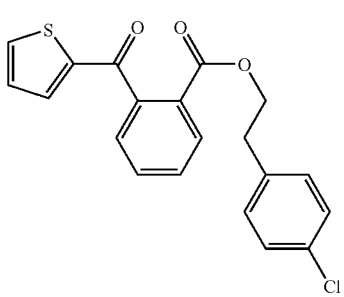 | 370.8 | 371.2 | 1.53 * 10E−6 | n.m. | B: 24.75' | 72.5 | n.m. |

-continued
| Example | Structure | $M_r$ (g/mol) | ESI-MS $(M + H^+)$ | $IC_{50}$ (M) | $K_i$ (M) | Gradient and time of retention for HPLC[a] | Extra-cellular IL-6 concentration[b], % of untreated cells | Extra-cellular Aβ-concentration, % of control |
|---|---|---|---|---|---|---|---|---|
| 38 | 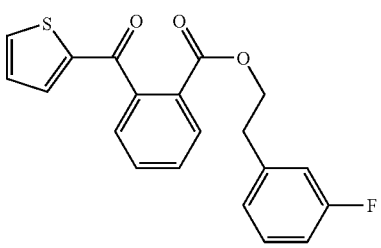 | 354.4 | 355.3 | 7.59 * 10E−8 | 9.75 * 10E−9 | B: 21.70' | 33.0 | n.m. |
| 39 | 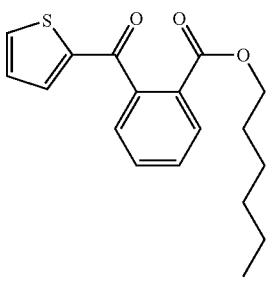 | 316.4 | 317.3 | 3.02 * 10E−7 | 3.41 * 10E−8 | C: 14.68' | 50.2 | n.m. |
| 40 | 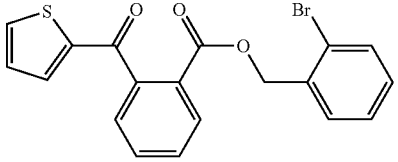 | 401.3 | 402.2 | 7.23 * 10E−7 | 1.51 * 10E−7 | C: 24.39' | 36.0 | n.m. |
| 41 | 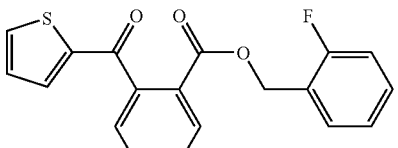 | 340.4 | 341.2 | 4.14 * 10E−7 | 4.24 * 10E−8 | C: 15.64' | 46.4 | n.m. |
| 42 | 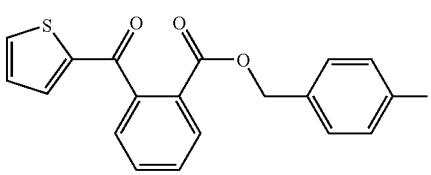 | 340.4 | 341.2 | 3.42 * 10E−7 | 2.54 * 10E−8 | C: 15.37' | 32.4 | n.m. |
| 43 | 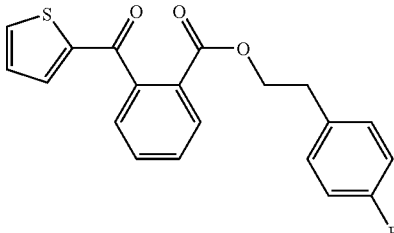 | 354.4 | 355.2 | 1.85 * 10E−7 | 1.52 * 10E−7 | B: 23.55' | 29.2 | n.m. |

-continued

| Example | Structure | $M_r$ (g/mol) | ESI-MS $(M + H^+)$ | $IC_{50}$ (M) | $K_i$ (M) | Gradient and time of retention for HPLC[a] | Extra-cellular IL-6 concentration[b], % of untreated cells | Extra-cellular Aβ-concentration, % of control |
|---|---|---|---|---|---|---|---|---|
| 44 | 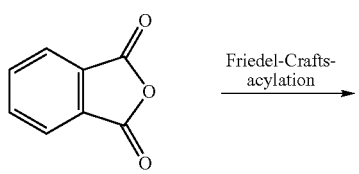 | 391.3 | 392.1 | 5.61 * 10E−7 | n.m. | C: 14.89' | 26.5 | n.m. |
| 45 | 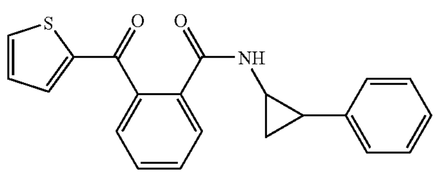 | 347.4 | 348.0 | 9.10 * 10E−5 | n.m. | B: 19.84' | 22.0 | n.m. |
| 46 | 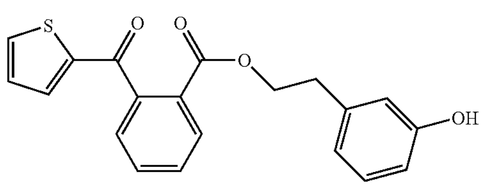 | 352.4 | 353.2 | 1.24 * 10E−7 | 1.39 * 10E−7 | C: 8.11' | 35.8 | n.m. |

[a]described in experimental section, [b]calculated with the untreated control sample as basal level, n.i. = no inhibition, n.m. = not measured.

General Synthetic Method

Intermediates: Intermediates I-IV were prepared via Friedel-Crafts acylation according to the procedure (scheme 1) from the literature (23): 2-(Furan-2-yl-carbonyl)-benzoic acid I, 2-(Thiophen-2-yl-carbonyl)-benzoic acid II, or analogue to this procedure trans-2-(Thiophen-2-yl-carbonyl)-1-cyclohexane carboxylic acid III, cis-2-(Thiophen-2-yl-carbonyl)-1-cyclohexane carboxylic acid IV.

Scheme 1

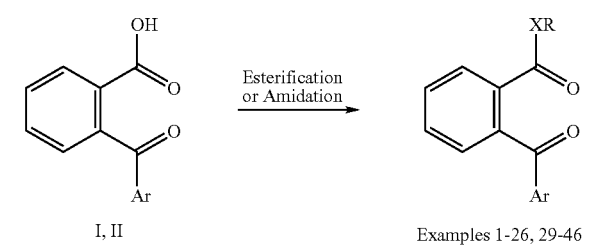

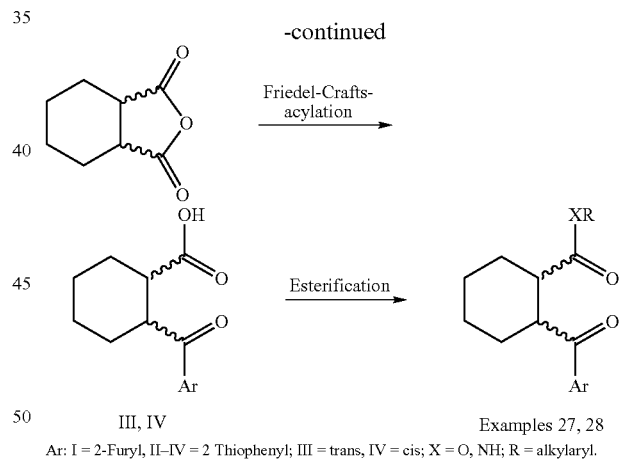

Ar: I = 2-Furyl, II–IV = 2 Thiophenyl; III = trans, IV = cis; X = O, NH; R = alkylaryl.

Esters: These examples (1-28, 33-44 and 46) were prepared in the manner of parallel synthesis. A typical batch is described as follows: 1.3 mmol of starting material I-IV and 1.3 mmol of the corresponding alcohol were dissolved in dry toluene (8 ml), 10 ul of concentrated sulphuric acid was added and the mixture was heated to 130° C. for 2 h by shaking the mixtures. After cooling to room temperature the discrete mixture was washed with saturated NaHCO₃-solution in order to remove the sulphuric acid. The organic solvent was separated, dried over Na₂SO₄, filtered and evaporated. The crude compound was purified by flash chromatography.

Amides: These examples (29-32 and 45) were prepared by a typical coupling reaction of starting material I or II and the corresponding amine, using N-methylmorpholine (NMM) and isobutyl chloroformate (CAIBE). After a typical workup the crude compound was purified by flash chromatography.

Compounds with other moieties than group (II) or phenyl of core A in formula 1 can be synthesized according to scheme 2.

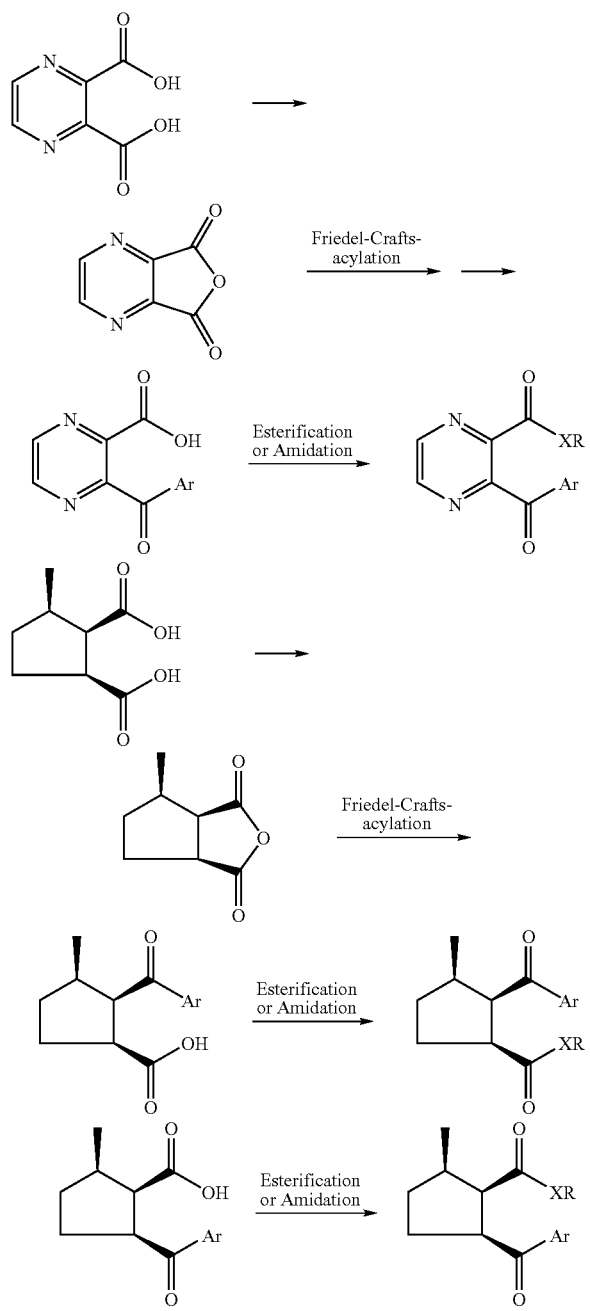

Ar = 2-Furyl or 2-Thiophenyl; X = O or NH; R = alkylaryl.

Analytical Methods

NMR spectra were performed on a Bruker AM 400 spectrometers. The following abbreviations are used: s (singlet), d (doublet), dd (doublet of doublets), t (triplet), and m (multiplet). ESI-MS: Mass spectra were taken with an MDS Sciex API 365 mass spectrometer equipped with an Ionspray™ interface (MDS Sciex; Thorn Hill, ON, Canada). The instrument settings, data acquisition and processing were controlled by the Applied Biosystems (Foster City, Calif., USA) Analyst™ software for Windows NT™. 50-100 scans were performed by the positive ionization Q1 scan mode to accumulate the peaks. Sample solutions were diluted with 50% methanol in 0.5% formic acid to reach concentrations about 10 µg/ml. Each sample solution was introduced directly by a microsyringe (1 ml) through an infusion pump (Havard Apperatus 22; Havard Instruments; Holliston, Mass., USA) and fused silica capillary tubing at a rate of 20 ul/min. Thin layer chromatography (TLC) was done using Macherey Nagel Polygram® SIL G/UV$_{245}$. Visualisation was accomplished by means of UV light at 254 nm, followed by dyeing with potassium permanganate or ninhydrin. Solvents were distilled prior to use. All commercially available reagents were used without further purification. Analytical HPLC was performed using a Merck-Hitachi device: acetonitrile-water (flow rate: 1 ml min$^{-1}$), column: LiChrosphere 5 um RP18e, 125×4.0 mm (Merck), pump: L-7100 Merck-Hitachi was used. Gradient A and B were used for the detection of the purified compounds in the examples. Characterisation of gradient A: starting from acetonitrile-water (20/80) at t=0 min to acetonitrile-water (95/5) within 30 min; characterisation of gradient B: starting from acetonitrile-water (5/95) at t=0 min to acetonitrile-water (60/40) within 20 min, to acetonitrile-water (95/5) after additional 10 min; characterisation of gradient C: starting from acetonitrile-water (40/60) at t=0 min to acetonitrile-water (95/5) within 20 min, remaining at acetonitrile-water (95/5) for additional 10 min.

Specific Synthesis and Analytical Information for Starting Materials and Certain Compounds Intermediate I 2-(Furan-2-yl-carbonyl)-benzoic acid Phthalic anhydrid (5.00 g, 33.8 mmol) was dissolved in dry CH$_2$Cl$_2$ and cooled to 0° C. AlCl$_3$ (5.33 g, 40.0 mmol) was added in portions in order to control the progress of the reaction. After stirring the mixture for 10 min a solution of thiophene (2.04 g, 2.77 ml, 35.0 mmol) in dry CH$_2$Cl$_2$ was added. After stirring the red solution overnight at room temperature, the reaction mixture was poured on an HCl solution/ ice mixture. After warming up to room temperature, the organic components were extracted with CHCl$_3$ (3×40 ml). The extracts were combined, washed with a 5% K$_2$CO$_3$ solution (40 ml) and acidified using diluted HCl solution. The solution was dried over Na$_2$SO$_4$ and concentrated under reduced pressure. The obtained residue was purified by flash chromatography, generating the desired compound (1.07 g, 14%).

Intermediate II 2-(Thiophen-2-yl-carbonyl)-benzoic acid

This compound was prepared according to the procedure described above for Intermediate 1, yield of the isolated compound: 30%.

Intermediate III trans-2-(Thiophen-2-yl-carbonyl)-1-cyclohexane carboxylic acid

This compound was prepared according to the procedure described above for Intermediate I, yield of the isolated compound: 38%.

Intermediate IV cis-2-(Thiophen-2-yl-carbonyl)-1-cyclohexane carboxylic acid

This compound was prepared according to the procedure described above for Intermediate I, yield of the isolated compound: 42%.

Example 4

2-(Fluorenyl-methyl-oxycarbonyl)-phenylthenon

To a solution of 2-(Thiophen-2-yl-carbonyl)-benzoic acid (302 mg, 1.3 mmol) and 9-Fluorenylmethanol (255 mg, 1.3 mmol) in dry toluol (8 ml) were added 10 μl of concentrated sulphuric acid. The mixture was heated to 130° C. for 2 h by shaking the mixture. After cooling to room temperature the mixture was washed with saturated $NaHCO_3$-solution in order to remove the sulphuric acid. The organic solvent was separated, dried over $Na_2SO_4$, filtered and evaporated. The crude compound was purified by flash chromatography to give the desired compound (100 mg, 19%).

$^1$H NMR (500 MHz, $CDCl_3$): δ=4.14 (t, 1H, CH), 4.37 (d, 2H, $CH_2$), 7.05 (dd, 1H, Aryl-H), 7.23-7.27 (m, 2H, Aryl-H), 7.33 (dd, 1H, Aryl-H), 7.36 (t, 2H, Aryl-H), 7.47 (dd, 2H, Aryl-H), 7.53 (td, 1H, Aryl-H), 7.60 (dt, 1H, Aryl-H), 7.64-7.67 (m, 2H, Aryl-H), 7.73 (d, 2H, Aryl-H), 8.02 (td, 1H, Aryl-H). -$^{13}$H NMR (125 MHz, $CDCl_3$): δ=46.60, 67.73, 119.93, 125.04, 127.11, 127.74, 127.91, 128.10, 129.29, 130.05, 130.26, 132.28, 134.44, 134.60, 141.17, 141.19, 143.61, 144.21, 166.03, 188.97. MS (EI) m/z (%): 411.3 ($M+H^+$), 428.3 ($M+NH_4^+$), 433.4 ($M+Na^+$), 449.2 ($M+K^+$).

Example 5

2-(4-Nitrophenyl-ethyl-oxycarbonyl)-phenylthenon

This compound was prepared according to the procedure described for Example 4, yield of the isolated compound: 56%. $^1$H NMR (500 MHz, $CDCl_3$): δ=2.94 (t, 2H, $CH_2$), 4.35 (t, 2H, $CH_2$), 7.05 (dd, 1H, Aryl-H), 7.25-7.46 (m, 3H, Aryl-H), 7.46 (td, 1H, Aryl-H), 7.55 (dt, 1H, Aryl-H), 7.61 (dt, 1H, Aryl-H), 7.68 (dd, 1H, Aryl-H), 7.94 (dd, 1H, Aryl-H), 8.07 (dd, 2H, Aryl-H). -$^{13}$H NMR (125 MHz, $CDCl_3$): δ=34.43, 64.90 123.65, 127.84, 128.16, 129.03, 129.59, 130.03, 130.30, 132.26, 134.54, 134.59, 140.82, 144.43, 145.38, 146.80, 165.93, 188.77. MS (EI) m/z (%): 382.2 ($M+H^+$), 399.2 ($M+NH_4^+$), 404.3 ($M+Na^+$), 420.2 ($M+K^+$).

Example 7

2-([2,3-Dihydro-1H-indene-2-yl]-oxycarbonyl)-phenylthenon

This compound was prepared according to the procedure described for Example 4, yield of the isolated compound: 18%. $^1$H NMR (500 MHz, $CDCl_3$): δ=2.85 (dd, 2H, $CH_2$), 3.21 (dd, 2H, $CH_2$), 5.52-5.56 (m, 1H, CH), 6.98 (dd, 1H, Aryl-H), 7.12 (s, 4H, Aryl-H), 7.18 (dd, 1H, Aryl-H), 7.41 (dd, 1H, Aryl-H), 7.52 (dt, 1H, Aryl-H), 7.57-7.60 (m, 2H, Aryl-H), 8.00 (dd, 1H, Aryl-H). -$^{13}$H NMR (125 MHz, $CDCl_3$): δ=39.03, 76.67, 124.52, 126.60, 127.56, 127.90, 129.25, 129.74, 130.34, 132.11, 134.31, 134.44, 140.06, 141.02, 144.47, 165.87, 188.91. MS (EI) m/z (%): 349.3 ($M+H^+$), 366.3 ($M+NH_4^+$), 387.3 ($M+K^+$).

Example 10

2-(Isoindolinyl-1,3-dione-ethyl-oxycarbonyl)-phenylthenon

This compound was prepared according to the procedure described for Example 4, yield of the isolated compound: 41%. $^1$H NMR (500 MHz, $CDCl_3$): δ=3.93 (t, 2H, $CH_2$), 4.34 (t, 2H, $CH_2$), 6.97 (dd, 1H, Aryl-H), 7.21 (dd, 1H, Aryl-H), 7.41 (dd, 1H, Aryl-H), 7.54 (dt, 1H, Aryl-H), 7.57-7.61 (m, 2H, Aryl-H), 7.70 (dd, 2H, Aryl-H), 7.83 (dd, 2H, Aryl-H), 8.00 (dd, 1H, Aryl-H). -$^{13}$H NMR (125 MHz, $CDCl_3$): δ=36.73, 62.53, 123.37, 127.61, 127.99, 128.63, 129.88, 130.48, 132.00, 132.30, 134.01, 134.33, 141.30, 144.39, 165.49, 167.90, 188.98. MS (EI) m/z (%): 406.4 ($M+H^+$), 423.3 ($M+NH_4^+$), 444.3 ($M+K^+$).

Example 13

2-(Furyl-methyl-oxycarbonyl)-phenylthenon

This compound was prepared according to the procedure described for Example 4, yield of the isolated compound: 7%. $^1$H NMR (500 MHz, $CDCl_3$): δ=5.08 (s, 3H, $CH_3$), 6.28-6.30 (m, 2H, Aryl-H), 7.01 (dd, 1H, Aryl-H), 7.22 (dd, 1H, Aryl-H), 7.33 (dd, 1H, Aryl-H), 7.44 (dd, 1H, Aryl-H), 7.53 (dt, 1H, Aryl-H), 7.60 (dt, 1H, Aryl-H), 7.64 (dd, 1H, Aryl-H), 8.02 (td, 1H, Aryl-H). -$^{13}$H NMR (125 MHz, $CDCl_3$): δ=58.93, 101.51, 110.91, 126.73, 127.72, 127.96, 128.83, 129.80, 130.44, 134.31, 134.35, 141.31, 143.26, 144.57, 148.72, 165.00, 188.96. MS (EI) m/z (%): 313.2 ($M+H^+$), 330.3 ($M+NH_4^+$), 335.2 ($M+Na^+$), 351.2 ($M+K^+$).

Example 14

2-(Thienyl-ethyl-oxycarbonyl)-phenylthenon

This compound was prepared according to the procedure described for Example 4, yield of the isolated compound: 29%. $^1$H NMR (400 MHz, $CDCl_3$): δ=2.84 (t, 2H, $CH_2$), 4.29 (t, 2H, $CH_2$), 6.87 (dd, 1H, Aryl-H), 6.91-6.92 (m, 1H, Aryl-H), 7.05 (dd, 1H, Aryl-H), 7.21 (dd, 1H, Aryl-H), 7.26 (dd, 1H, Aryl-H), 7.46 (dd, 1H, Aryl-H), 7.53-7.63 (m, 2H, Aryl-H), 7.67 (dd, 1H, Aryl-H), 8.00 (dd, 1H, Aryl-H). -$^{13}$H NMR (100 MHz, $CDCl_3$): δ=29.16, 65.39, 121.55, 125.52, 127.71, 128.05, 128.10, 129.32, 129.85, 130.27, 132.12, 134.31, 134.32, 137.60, 141.03, 144.64, 165.87, 188.86. MS (EI) m/z (%): 343.0 ($M+H^+$), 360.2 ($M+NH_4^+$), 365.2 ($M+Na^+$), 381.2 ($M+K^+$).

Example 15

2-(Phenyl-ethyl-oxycarbonyl)-1-(furylcarbonyl)-benzol

This compound was prepared according to the procedure described for Example 4, yield of the isolated compound: 41%. $^1$H NMR (500 MHz, $CDCl_3$): δ=2.82 (t, 2H, $CH_2$), 4.29 (t, 2H, $CH_2$), 6.50 (dd, 1H, Aryl-H), 6.95 (d, 1H, Aryl-H), 7.14 (d, 2H, Aryl-H), 7.18-7.21 (m, 1H, Aryl-H), 7.24-7.27 (m, 2H, Aryl-H), 7.48 (dd, 1H, Aryl-H), 7.53-7.62 (m, 3H, Aryl-H), 7.96 (dd, 1H, Aryl-H). -$^{13}$H NMR (125 MHz, CDCl$_3$): δ=34.64, 66.03, 112.36, 119.08, 126.54, 128.04, 128.46, 12.82, 129.82, 130.03, 130.17, 132.15, 137.38, 140.01, 146.96, 152.74, 166.08, 184.09. MS (EI) m/z (%): 321.3 (M+H$^+$), 338.3 (M+NH$_4^+$), 343.1 (M+Na$^+$), 359.2 (M+K$^+$).

Example 16

2-(4-Methylphenylethyl-oxycarbonyl)-phenylthenon

This compound was prepared according to the procedure described for Example 4, yield of the isolated compound: 30%. $^1$H NMR (500 MHz, CDCl$_3$): δ=2.28 (s, 3H, CH$_3$), 2.76 (t, 2H, CH$_2$), 4.25 (t, 2H, CH$_2$), 6.99 (d, 2H, Aryl-H), 7.05 (dd, 3H, Aryl-H), 7.26 (dd, 1H, Aryl-H), 7.46 (dd, 1H, Aryl-H), 7.54 (dd, 1H, Aryl-H), 7.60 (dd, 1H, Aryl-H), 7.67 (dd, 1H, Aryl-H), 7.98 (td, 1H, Aryl-H). -$^{13}$H NMR (125 MHz, CDCl$_3$): δ=20.98, 34.13, 66.19, 127.69, 128.07, 128.70, 129.13, 129.36, 129.86, 130.28, 132.13, 134.28, 134.38, 136.02, 140.99, 144.66, 165.92, 189.04. MS (EI) m/z (%): 351.3 (M+H$^+$), 368.2 (M+NH$_4^+$), 373.1 (M+Na$^+$), 389.2 (M+K$^+$).

Example 19

2-(4-Chlorophenyl-methyl-oxycarbonyl)-phenylthenon

This compound was prepared according to the procedure described for Example 4, yield of the isolated compound: 13%. $^1$H NMR (400 MHz, CDCl$_3$): δ=5.08 (s, 2H, CH$_2$), 7.00 (dd, 1H, Aryl-H), 7.12 (d, 2H, Aryl-H), 7.20-7.23 (m, 3H, Aryl-H), 7.45 (dd, 1H, Aryl-H), 7.53-7.65 (m, 3H, Aryl-H), 8.04 (dd, 1H, Aryl-H). -$^{13}$H NMR (125 MHz, CDCl$_3$): δ=66.53, 127.75, 128.02, 128.65, 128.89, 129.34, 129.75, 129.91, 130.48, 130.67, 132.37, 133.57, 134.40, 134.44, 134.52, 164.34, 188.88. MS (EI) m/z (%): 357.2 (M+H$^+$), 374.1 (M+NH$_4^+$), 379.3 (M+Na$^+$), 395.1 (M+K$^+$).

Example 24

2-(Benzo[b]thiophen-2-yl-ethyl-oxycarbonyl)-phenylthenon

This compound was prepared according to the procedure described for Example 4, yield of the isolated compound: 19%. $^1$H NMR (500 MHz, CDCl$_3$): δ=3.04 (dt, 2H, CH$_2$), 4.29 (t, 2H, CH$_2$), 7.00 (dd, 1H, Aryl-H), 7.06 (s, 1H, Aryl-H), 7.24 (dd, 1H, Aryl-H), 7.30-7.37 (m, 2H, Aryl-H), 7.47 (td, 1H, Aryl-H), 7.55 (dt, 1H, Aryl-H), 7.60-7.63 (m, 2H, Aryl-H), 7.69 (td, 1H, Aryl-H), 7.82 (ddd, 1H, Aryl-H), 7.99 (ddd, 1H, Aryl-H). -$^{13}$H NMR (125 MHz, CDCl$_3$): δ=27.39, 64.29, 121.45, 122.76, 122.82, 123.99, 124.27, 127.72, 128.11, 129.18, 129.91, 130.36, 131.73, 132.24, 134.44, 138.67, 140.29, 140.97, 144.61, 165.98, 189.01. MS (EI) m/z (%): 393.2 (M+H$^+$), 415.2 (M+Na$^+$), 431.2 (M+K$^+$).

Example 27 trans-1-(Thienylcarbonyl)-2-(phenyl-ethyl-oxycarbonyl)-cyclohexane

This compound was prepared according to the procedure described for Example 4, yield of the isolated compound: 21%. $^1$H NMR (400 MHz, CDCl$_3$): δ=1.35-1.45 (m, 3H, CH$_2$), 1.78-1.83 (m, 2H, CH$_2$), 2.76-2.82 (m, 2H, CH$_2$), 2.84-2.90 (m, 3H, CH$_2$), 3.34-3.40 (m, 1H, CH$_2$), 4.13-4.24 (m, 3H, CH$_2$), 7.08-7.27 (m, 6H, Aryl-H), 7.61 (dd, 1H, Aryl-H), 7.73 (dd, 1H, Aryl-H). -$^{13}$H NMR (100 MHz, CDCl$_3$): δ=25.37, 25.54, 29.00, 30.32, 34.93, 44.53, 48.52, 64.91, 126.43, 128.06, 128.34, 128.88, 131.35, 131.85, 133.53, 137.72, 174.88, 195.60. MS (EI) m/z (%): 343.2 (M+H$^+$), 360.4 (M+NH$_4^+$), 365.3 (M+Na$^+$), 381.3 (M+K$^+$).

Example 29

2-(Phenylmethyl-amincarbonyl)-phenylthenon

NMM (131 mg, 143 µl, 1.3 mmol) was added to a stirred and cooled solution (−15° C.) of 2-(Thiophen-2-yl-carbonyl)-benzoic acid (302 mg, 1.3 mmol) in dry THF (4 ml). Isobutyl chloroformate (178 mg, 170 µl, 1.3 mmol) was added dropwise. After stirring for 15 minutes, benzylamine (139 mg, 142 µl, 1.3 mmol) in dry THF (2 ml) was added and the mixture was stirred 14 h, during which time it was allowed to warm to room temperature. The solvent was evaporated in vacuo and the obtained residue was dissolved in ethyl acetate (10 ml), washed with 1N HCl, water, aqueous NaHCO$_3$, water and brine (5 ml per washing step) and dried over Na$_2$SO$_4$. After filtration the solvent was evaporated under reduced pressure. The crude compound was purified by flash chromatography to give the desired product (280 mg, 67%).

The invention claimed is:

1. A compound of the general formula 1, or a pharmaceutically acceptable salt thereof, including all stereoisomers thereof:

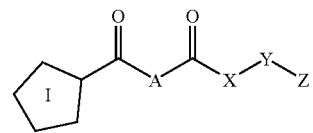
(1)

wherein

I is furyl or thienyl in either case optionally substituted by one or more groups selected from (i) hydroxyl, nitro, halogen and cyano and (ii) methyl, ethyl, methoxy, and ethoxy wherein one or more hydrogen atoms of said groups is optionally substituted by halogen (e.g. fluorine);

A is selected from a group of formula (I) to (VI):

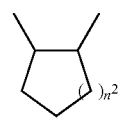
(II)

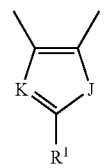
(III)

-continued

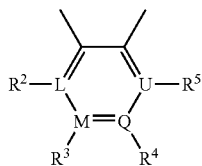
(IV)

wherein:
n² is an integer 1-3;
R¹-R⁵ are independently H, alkyl, alkenyl, alkynyl, carbocycle, aryl, -alkylaryl, heterocycle, heteroaryl or -alkylheteroaryl;
J is CR¹¹R¹², wherein R¹¹ and R¹² are independently H, alkyl, alkenyl, alkynyl, carbocycle, aryl, alkylaryl, heterocycle, heteroaryl or alkylheteroaryl, or R¹¹ and R¹² can be connected to form a carbocyclic ring with up to 7 members (e.g. a 5- or 6-membered ring);
K is CR¹³, wherein R¹³ is H, alkyl, alkenyl, alkynyl, carbocycle, aryl, -alkylaryl, heterocycle, heteroaryl or -alkylheteroaryl;
L, M, Q, U are C;
X is NR¹⁴ or O, wherein R¹⁴ is H, alkyl, alkenyl, alkynyl, carbocycle, aryl, -alkylaryl, heterocycle, heteroaryl or -alkylheteroaryl;
Y is alkyl, alkenyl, alkynyl, carbocycle, aryl, heterocycle, heteroaryl or a bond; and
Z is a carbocycle, aryl, heterocycle or heteroaryl.

2. A compound according to claim 1, wherein I represents 2-furyl.
3. A compound according to claim 1, wherein I represents thienyl.
4. A compound according to claim 3, wherein I represents 2-thienyl.
5. A compound according to claim 1, wherein A represents a group of formula (II).
6. A compound according to claim 5, wherein n² is 2.
7. A compound according to claim 1, wherein A represents a group of formula (III).
8. A compound according to claim 7, wherein R¹ represents Me or H.
9. A compound according to claim 8, wherein R¹ represents H.
10. A compound according to claim 7, wherein J represents CH₂.
11. A compound according to claim 7, wherein K represents CH.
12. A compound according to claim 1, wherein A represents a group of formula (IV).
13. A compound according to claim 12, wherein L-R² represents CH or CMe.
14. A compound according to claim 13, wherein L-R² represents CH.
15. A compound according to claim 12, wherein M-R³ represents CH or CMe.
16. A compound according to claim 15, wherein M-R³ represents CH.
17. A compound according to claim 12, wherein Q-R⁴ represents CH or CMe.
18. A compound according to claim 17, wherein Q-R⁴ represents CH.
19. A compound according to claim 12, wherein U—R⁵ represents CH or CMe.

20. A compound according to claim 19, wherein U—R⁵ represents CH.
21. A compound according to claim 12, wherein L-R³, M-R⁴, U—R⁵ and U—R⁵ represent CH.
22. A compound according to claim 1, wherein X is O or NH.
23. A compound according to claim 22, wherein X is O.
24. A compound according to claim 1, wherein Y is a bond or represents CH₂, (CH₂)₂ or (CH₂)₃.
25. A compound according to claim 24, wherein Y represents (CH₂)₂.
26. A compound according to claim 24, wherein Y represents (CH₂)₃.
27. A compound according to claim 1, wherein Z represents optionally substituted phenyl or thienyl.
28. A compound according to claim 27, wherein Z represents a group selected from phenyl, 3-methylphenyl, 4-methylphenyl, 2-chlorophenyl, 3-chlorophenyl, 4-chlorophenyl, thien-2-yl and thien-3-yl.
29. A compound according to claim 27, wherein Z is 3-fluorophenyl.
30. A compound according to claim 1 selected from the group consisting of Formula (1) through (32), or a pharmaceutical salt, or stereoisomer thereof:

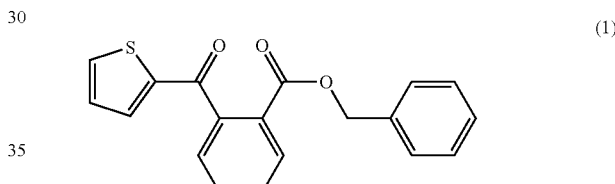
(1)

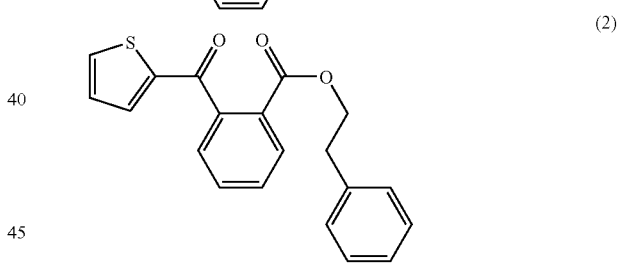
(2)

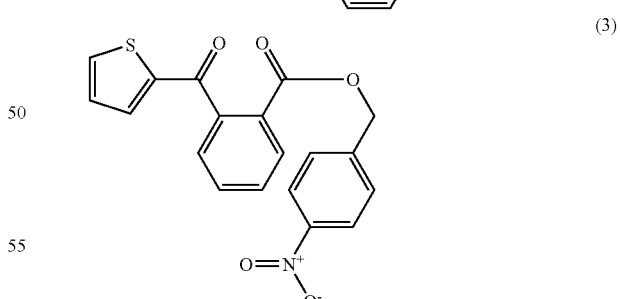
(3)

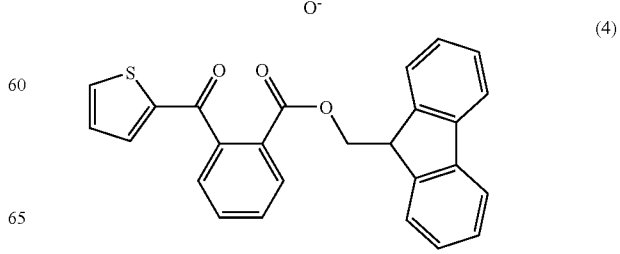
(4)

-continued

(16)
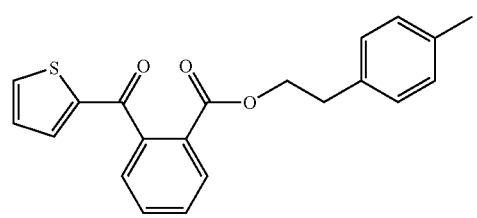
(17)
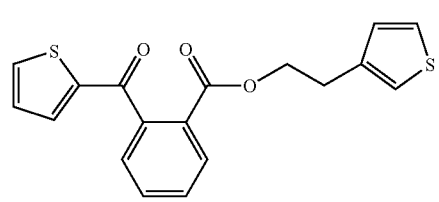
(18)
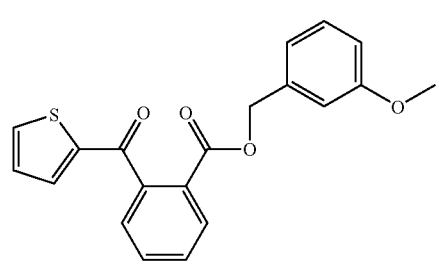
(19)
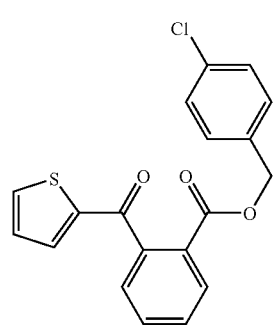
(20)
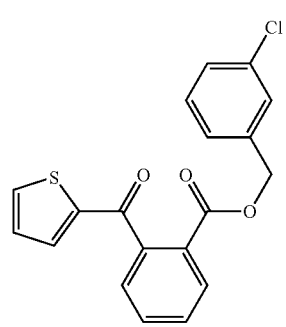
(21)
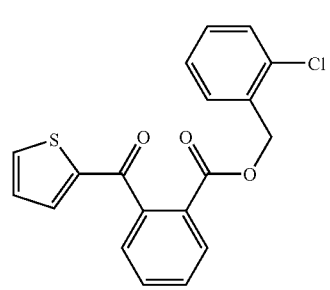
(22)
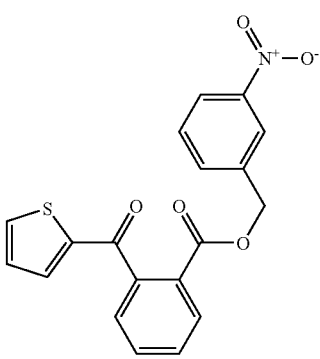
(23)
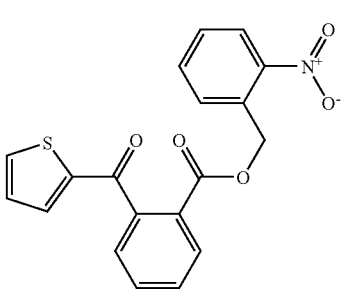
(24)
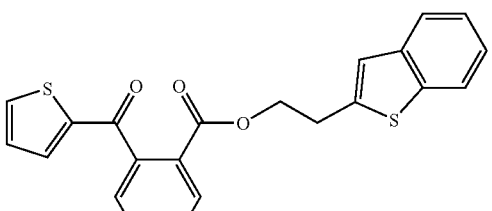
(25)
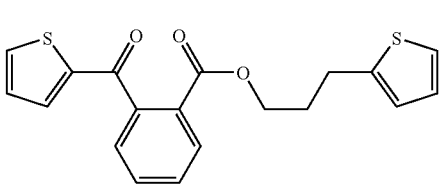
(26)
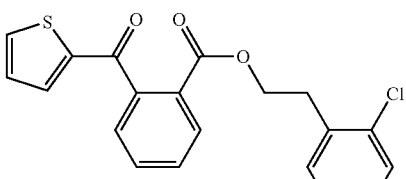
(27)
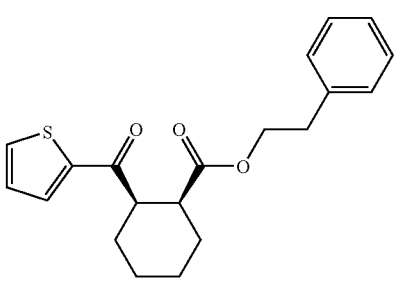

(28)
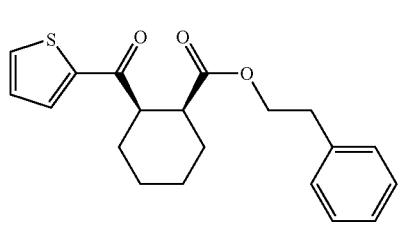
(29)
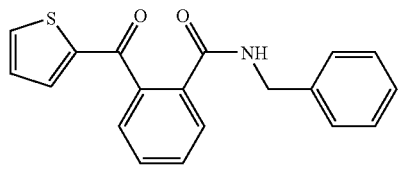
(30)
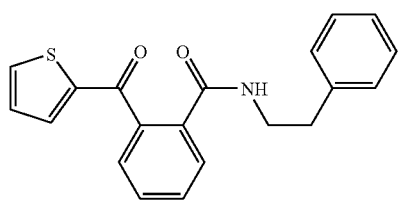
(31)
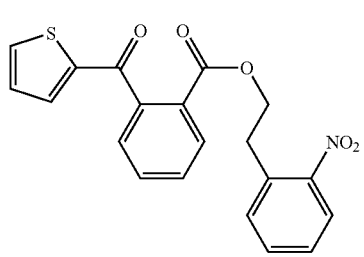
(32)
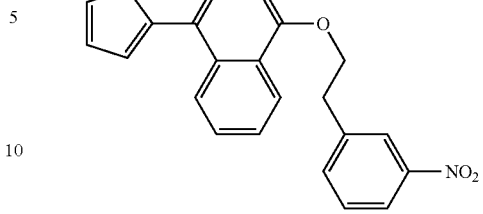
31. A compound according to claim 1 selected from the group consisting of Formula (33), (34), (35), (36), (37), (38), (39), (40), (41), (42), (43), (44), (45), and (46), or a pharmaceutical salt, stereoisomer thereof:
(33)
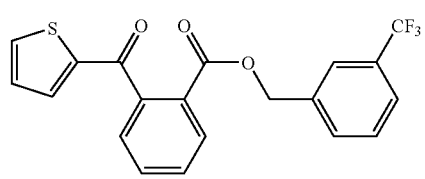
(34)
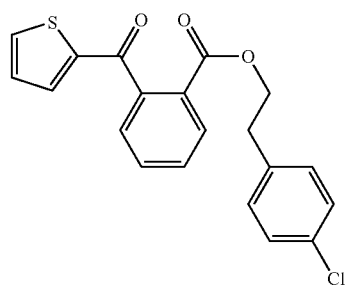
(35)
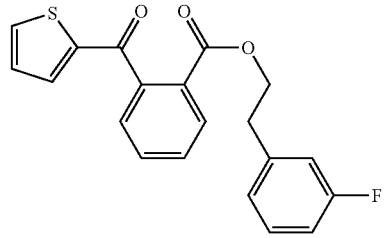
(36)
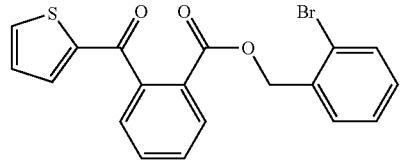
(37)
(38)
(40)
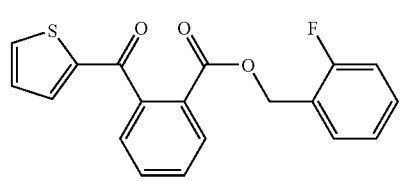
(41)

-continued

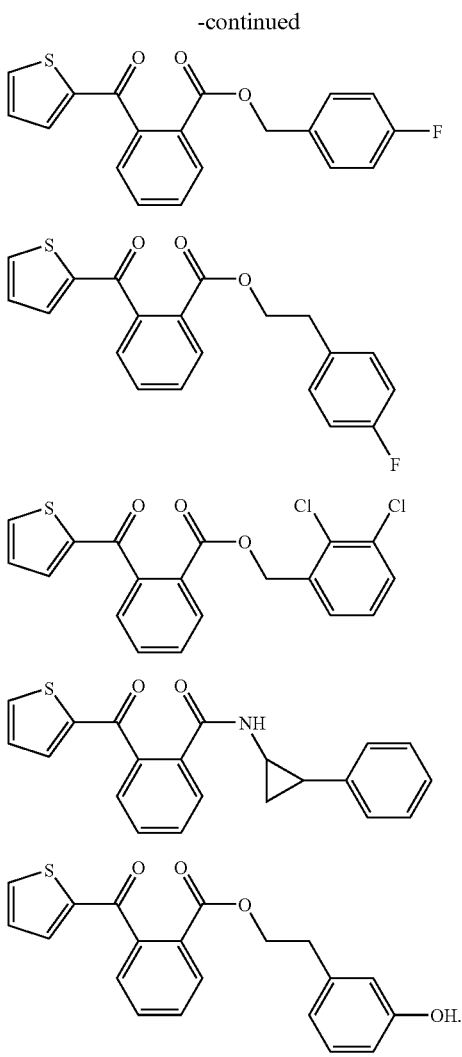

(42)
(43)
(44)
(45)
(46)

32. A compound according to claim 1 wherein

I is furyl or thienyl;

A is phenyl;

X is O or NH;

Y is alkyl or $C_3$-$C_5$ cycloalkyl; and

Z is 9-fluorene, phenyl, 3-methylphenyl, 4-methylphenyl, 2-thienyl, 3-thienyl, 2-chlorophenyl, 3-chlorophenyl, 4-chlorophenyl, 2,3-dichlorophenyl, 3-methoxyphenyl, 2-fluorophenyl, 3-fluorophenyl, 4-fluorophenyl, 2-bromophenyl or 3-hydroxyphenyl.

33. A compound according to claim 32, wherein I is 2-furyl or 2-thienyl.

34. A compound according to claim 32, wherein Y is $CH_2$, $CH_2CH_2$, $CH_2CH_2CH_2$ or

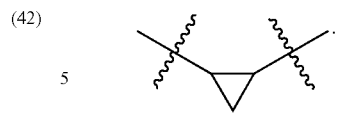

35. A compound according to claim 32, wherein Z is phenyl, 4-methylphenyl, 3-thienyl, 2,3-dichlorophenyl, 4-fluorophenyl or 3-hydroxyphenyl.

36. A compound according to claim 1 wherein

I is furyl or thienyl;

A is phenyl;

X is O or NH;

Y is alkyl or a bond; and

Z is 9-fluorene, 2-indanyl, phenyl, 3-methylphenyl, 4-methylphenyl, 2-thienyl, 3-thienyl, 2-chlorophenyl, 3-chlorophenyl, 4-chlorophenyl, 2-nitrophenyl, 3-nitrophenyl or 2-benzothienyl.

37. A compound of claim 36, wherein I is 2-furyl or 2-thienyl.

38. A compound according to claim 36, wherein Y is $CH_2$, $CH_2CH_2$, or $CH_2CH_2CH_2$.

39. A compound according to claim 36, wherein Z is 9-fluorene, 2-indanyl, phenyl, 3-methylphenyl, 2-thienyl, 3-thienyl, 2-chlorophenyl or 2-nitrophenyl.

40. A compound according to claim 32, wherein X is O.

41. A pharmaceutical composition comprising at least one compound according to claim 1 together with one or more therapeutically acceptable diluents or carriers.

42. A pharmaceutical composition according to claim 41 for parenteral, enteral or oral administration.

43. A pharmaceutical composition according to claim 41 which comprises additionally at least one compound selected from the group consisting of QC-inhibitors, LiCl, inhibitors of dipeptidyl aminopeptidases, preferably inhibitors of DP IV or DP IV-like enzymes, NPY-receptor ligands, NPY agonists, ACE inhibitors, PIMT enhancers, inhibitors of beta secretases, inhibitors of gamma secretases, inhibitors of neutral endopeptidase, PDE-4 inhibitors, MAO inhibitors, TNFalpha inhibitors, amyloid protein or amyloid peptide deposition inhibitors, sigma-1 receptor inhibitors and histamine H3 antagonists.

44. A process for preparing a compound of claim 1 comprising reacting a compound of formula (IA), with a compound of formula (IB):

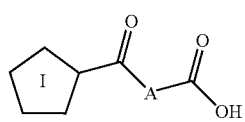

Formula (IA)

HX—Y-Z

Formula (IB)

wherein I, A, X, Y and Z are as defined in claim 1.

* * * * *